United States Patent

Schatz

Patent Number: 5,195,984
Date of Patent: Mar. 23, 1993

[54] EXPANDABLE INTRALUMINAL GRAFT

[75] Inventor: Richard A. Schatz, Paradise Valley, Ariz.

[73] Assignee: Expandable Grafts Partnership, San Antonio, Tex.

[21] Appl. No.: 657,296

[22] Filed: Feb. 19, 1991

Related U.S. Application Data

[63] Continuation of Ser. No. 253,115, Oct. 4, 1988, abandoned.

[51] Int. Cl.⁵ .......................................... A61M 29/00
[52] U.S. Cl. ................................. 606/195; 606/193; 606/194; 623/1; 604/104; 604/96
[58] Field of Search ................ 600/36; 604/96, 104; 606/193, 194, 195; 623/1, 12

[56] References Cited

U.S. PATENT DOCUMENTS

| | | | |
|---|---|---|---|
| 3,744,596 | 11/1973 | Cook | 128/343 |
| 4,512,338 | 4/1985 | Balko et al. | 128/341 |
| 4,553,545 | 11/1985 | Maass et al. | 128/341 |
| 4,733,665 | 3/1988 | Palmaz | 623/1 |
| 4,739,762 | 4/1988 | Palmaz | 623/1 |
| 4,760,849 | 8/1988 | Kropf | 128/343 |
| 4,776,337 | 10/1988 | Palmaz | 623/1 |
| 4,800,882 | 1/1989 | Gianturco | 128/343 |
| 4,856,516 | 8/1989 | Hillstead | 623/12 |
| 4,969,458 | 11/1990 | Wiktor | 606/194 |
| 5,102,417 | 4/1992 | Palmaz | 606/195 |
| 5,135,536 | 8/1992 | Hillstead | 606/195 |

OTHER PUBLICATIONS

"Self-Expanding Endovacular Graft: An Experimental Study in Dogs" 151 AJR 673-76, Oct. 1988 (first made available to the public on Sep. 20, 1988).

Primary Examiner—Paul Prebilic
Attorney, Agent, or Firm—Ben D. Tobor

[57] ABSTRACT

A plurality of expandable and deformable intraluminal vascular grafts are expanded within a blood vessel by an angioplasty balloon associated with a catheter to dilate and expand the lumen of a blood vessel. The grafts may be thin-walled tubular members having a plurality of slots disposed substantially parallel to the longitudinal axis of the tubular members, and adjacent grafts are flexibly connected by a single connector member disposed substantially parallel to the longitudinal axis of the tubular members.

6 Claims, 3 Drawing Sheets

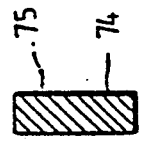
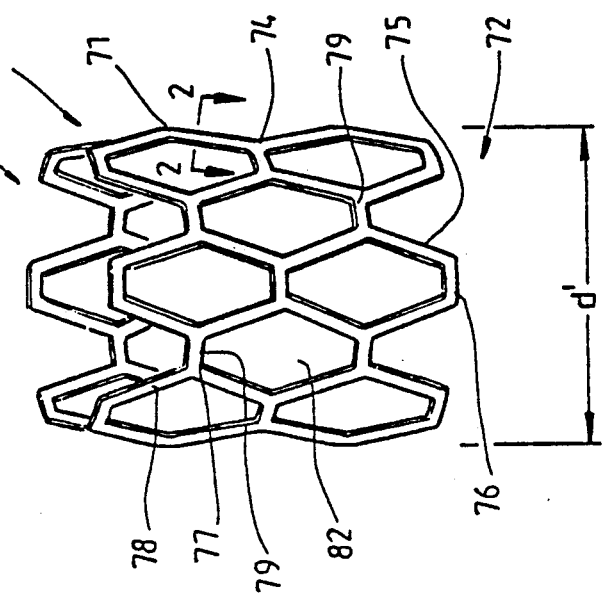
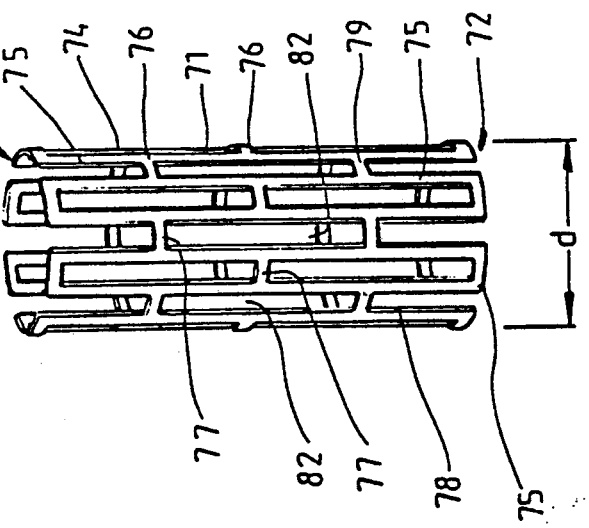

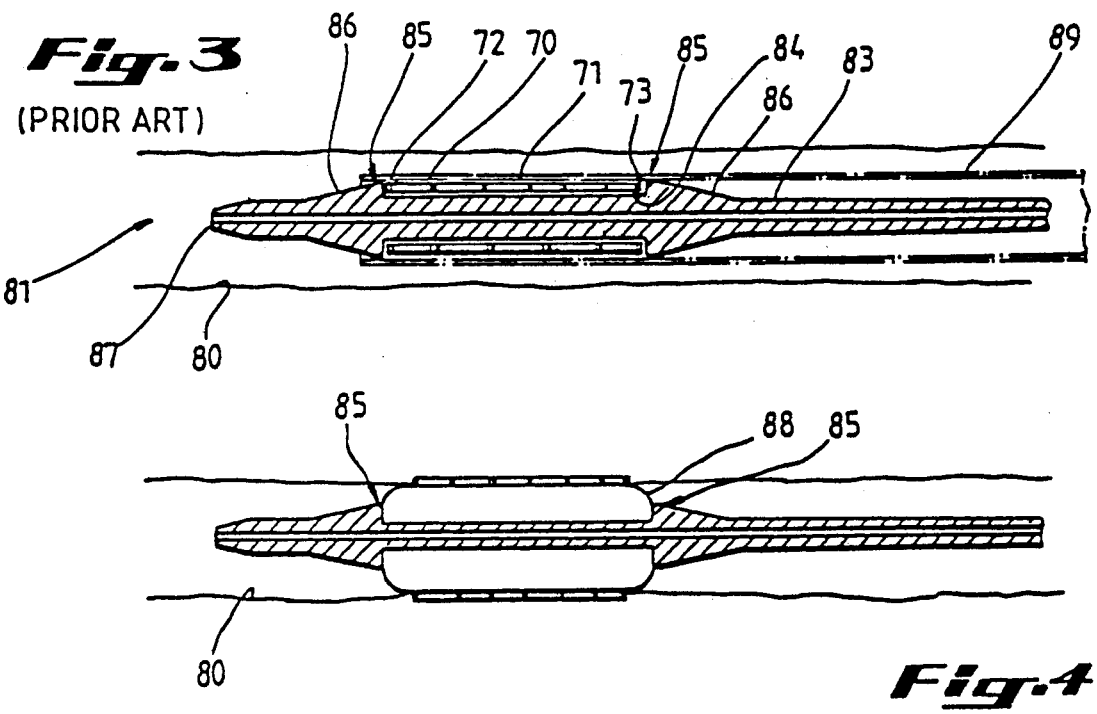
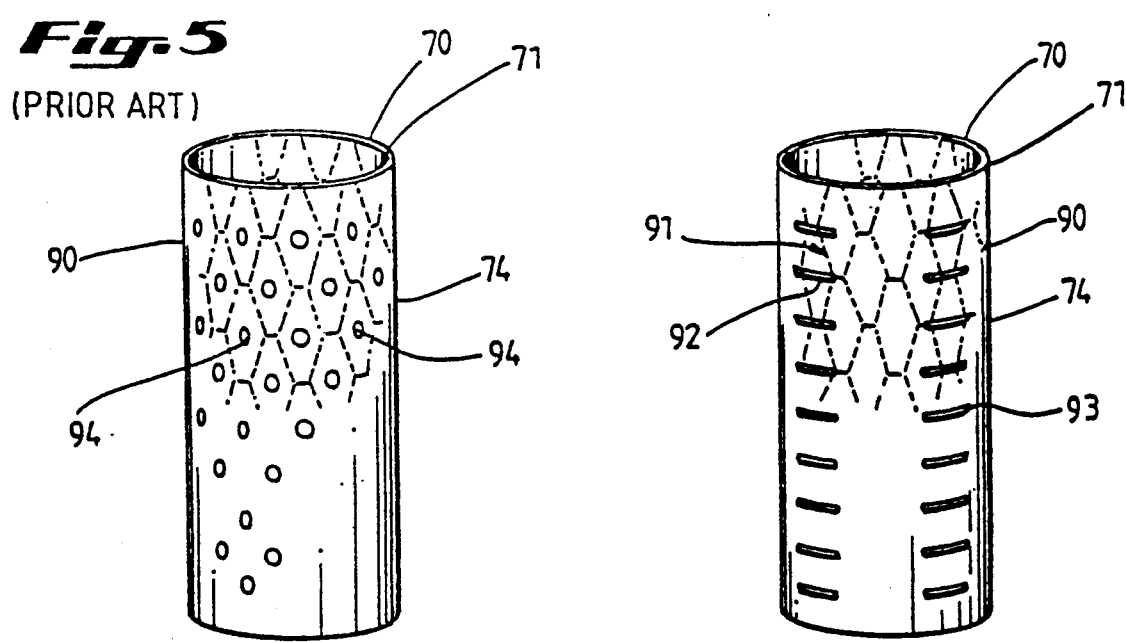

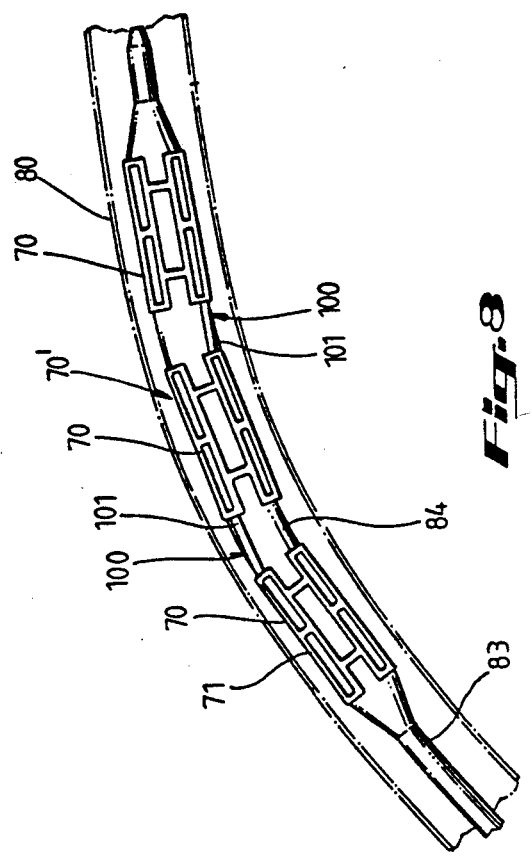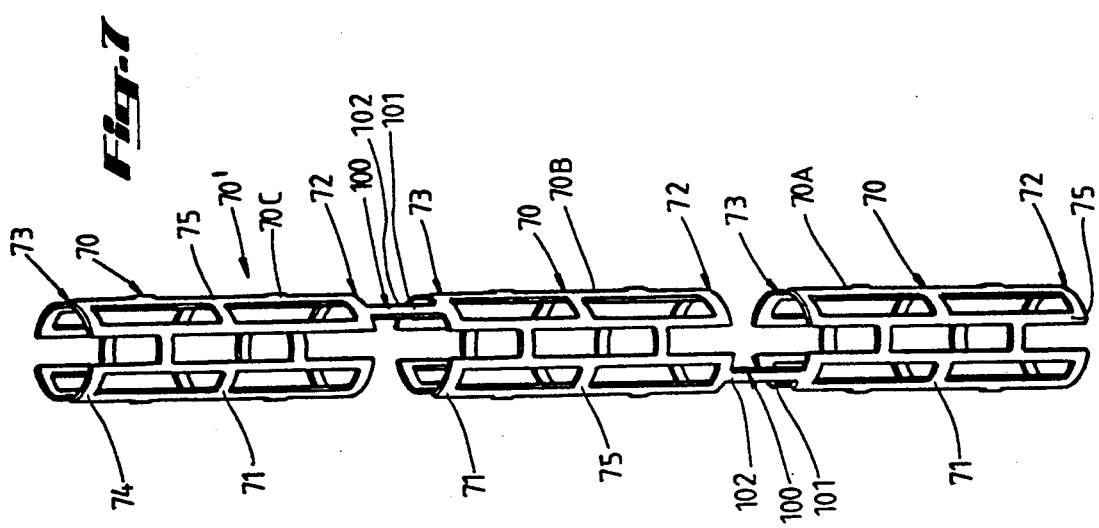

EXPANDABLE INTRALUMINAL GRAFT

This application is a division of application Ser. No. 07/253,115, filed Oct. 4, 1988 now abandoned.

1. Field of the Invention

The invention relates to an expandable intraluminal graft for use within a body passageway or duct and, more particularly, expandable intraluminal vascular grafts which are particularly useful for repairing blood vessels narrowed or occluded by disease; and a method and apparatus for implanting expandable intraluminal grafts.

2. Description of the Prior Art

Intraluminal endovascular grafting has been demonstrated by experimentation to present a possible alternative to conventional vascular surgery. Intraluminal endovascular grafting involves the percutaneous insertion into a blood vessel of a tubular prosthetic graft and its delivery via a catheter to the desired location within the vascular system. Advantages of this method over conventional vascular surgery include obviating the need for surgically exposing, incising, removing, replacing, or bypassing the defective blood vessel.

Structures which have previously been used as intraluminal vascular grafts have included coiled stainless steel springs; helically wound coil springs manufactured from an expandable heat-sensitive material: and expanding stainless steel stents formed of stainless steel wire in a zig-zag pattern. In general, the foregoing structures have one major disadvantage in common. Insofar as these structures must be delivered to the desired location within a given body passageway in a collapsed state, in order to pass through the body passageway, there is no effective control over the final, expanded configuration of each structure. For example, the expansion of a particular coiled spring-type graft is predetermined by the spring constant and modulus of elasticity of the particular material utilized to manufacture the coiled spring structure. These same factors predetermine the amount of expansion of collapsed stents formed of stainless steel wire in a zig-zag pattern. In the case of intraluminal grafts, or prostheses, formed of a heat sensitive material which expands upon heating, the amount of expansion is likewise predetermined by the heat expansion characteristics of the particular alloy utilized in the manufacture of the intraluminal graft.

Thus, once the foregoing types of intraluminal grafts are expanded at the desired location within a body passageway, such as within an artery or vein, the expanded size of the graft cannot be changed. If the diameter of the desired body passageway has been miscalculated, an undersized graft might not expand enough to contact the interior surface of the body passageway, so as to be secured thereto. It may then migrate away from the desired location within the body passageway. Likewise, an oversized graft might expand to such an extent that the spring force, or expansion force, exerted by the graft upon the body passageway could cause rupturing of the body passageway. Further, the constant outwardly radiating force exerted upon the interior surface of the body passageway can cause erosion of the internal surface, or intima, of the artery or body passageway.

Another alternative to conventional vascular surgery has been percutaneous balloon dilation of elastic vascular stenoses, or blockages, through use of a catheter mounted angioplasty balloon. In this procedure, the angioplasty balloon is inflated within the stenosed vessel, or body passageway, in order to shear and disrupt the wall components of the vessel to obtain an enlarged lumen. With respect to arterial atheroscleerotic lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or block the lumen. Typically, the distending intraluminal pressure within the body passageway can hold the disrupted layer or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct this problem.

Although the balloon dilation procedure is typically conducted in the catheterization lab of a hospital, because of the foregoing problem, it is always necessary to have a surgeon on call should the intimal flap block the blood vessel or body passageway. Further, because of the possibility of the intimal flap tearing away from the blood vessel and blocking the lumen, balloon dilations cannot be performed upon certain critical body passageways, such as the left main coronary artery, which leads into the heart. If an intimal flap formed by a balloon dilation procedure abruptly comes down and closes off a critical body passageway, such as the left main coronary artery, the patient could die before any surgical procedures could be performed.

Additional disadvantages associated with balloon dilation of elastic vascular stenoses is that many fail because of elastic recoil of the stenotic lesion. This usually occurs due to a high fibrocollagenous content in the lesion and is sometimes due to certain mechanical characteristics of the area to be dilated. Thus, although the body passageway may initially be successfully expanded by a balloon dilation procedure, subsequent, early restenosis can occur due to the recoil of the body passageway wall which decreases the size of the previously expanded lumen of the body passageway. For example, stenoses of the renal artery at the ostium are known to be refractory to balloon dilation because the dilating forces are applied to the aortic wall rather than to the renal artery itself. Vascular stenoses caused by neointimal fibrosis, such as those seen in dialysis-access fistulas, have proved to be difficult to dilate, requiring high dilating pressures and larger balloon diameters. Similar difficulties have been observed in angioplasties of graft-artery anastomotic strictures and postendarterectomy recurrent stenoses. Percutaneous angioplasty of Takayasu arteritis and neurofibromatosis arterial stenoses may show poor initial response and recurrence which is believed due to the fibrotic nature of these lesions.

For repairing blood vessels narrowed or occluded by disease, or repairing other body passageways, the length of the body passageway which requires repair, as by the insertion of a tubular prosthetic graft, may present problems if the length of the required graft cannot negotiate the curves or bends of the body passageway through which the graft is passed by the catheter. In other words, in many instances, it is necessary to support a length of tissue within a body passageway by a graft, wherein the length of the required graft exceeds the length of a graft which can be readily delivered via a catheter to the desired location within the vascular system. Some grafts do not have the requisite ability to bend so as to negotiate the curves and bends present within the vascular system, particularly prostheses or grafts which are relatively rigid and resist bending with respect to their longitudinal axes.

Accordingly, prior to the development of the present invention, there has been no expandable intraluminal vascular graft for expanding the lumen of a body passageway, which: prevents recurrence of stenoses in the body passageway; can be utilized for critical body passageways, such as the left main coronary artery of a patient's heart; prevents recoil of the body passageway wall; allows the intraluminal graft to be expanded to a variable size to prevent migration of the graft away from the desired location and prevents rupturing and/or erosion of the body passageway by the expanded graft; permits tissue of an elongated section of a body passageway to be supported by an elongated graft; and provides the necessary flexibility to negotiate the bends and curves in the vascular system. Therefore, the art has sought an expandable intraluminal vascular graft which: prevents recurrence of stenoses in the body passageway; is believed to be able to be utilized in critical body passageways, such as the left main coronary artery of the heart; prevents recoil of the body passageway; can be expanded to a variable size within the body passageway to prevent migration of the graft away from the desired location and to prevent rupturing and/or erosion of the body passageway by the expanded graft; permits tissue of an elongated section of a body passageway to be supported by an elongated graft; and provides the necessary flexibility to negotiate the bends and curves in the vascular system.

SUMMARY OF THE INVENTION

In accordance with the invention, the foregoing advantages have been achieved by the present expandable intraluminal vascular graft. The present invention includes a plurality of thin-walled tubular members, each having first and second ends and a wall surface disposed between the first and second ends, the wall surface having a substantially uniform thickness and a plurality of slots formed therein, the slots being disposed substantially parallel to the longitudinal axis of each tubular member; a single connector member being disposed between adjacent tubular members to flexibly connect adjacent tubular members, the single connector member being disposed in a substantially parallel relationship with respect to the longitudinal axis of the tubular members and coplanar with each tubular member; each tubular member having a first diameter which permits intraluminal delivery of the tubular members into a body passageway having a lumen; and the tubular members having a second, expanded and deformed diameter, upon the application from the interior of the tubular members of a radially, outwardly extending force, which second diameter is variable and dependent upon the amount of force applied to the tubular members, whereby the tubular members may be expanded and deformed to expand the lumen of the body passageway.

A further feature of the present invention is that the single connector member may be a thin-walled, elongate bar member, coplanar with adjacent tubular members. An additional feature of the present invention is that a first connector member may be disposed between the second end of a first tubular member and the first end of a second tubular member; a second connector member may be disposed between the second end of the second tubular member and the first end of a third tubular member; the first and second connector members being angularly offset from one another with respect to the longitudinal axis of the tubular members.

The expandable intraluminal vascular graft of the present invention, when compared with previously proposed prior art intraluminal grafts, has the advantages of: preventing recurrence of stenoses; is believed to permit implantation of grafts in critical body passageways, such as in the left main coronary artery of the heart; prevents recoil of the body passageway; prevents erosion of the body passageway by the expanded graft; permits expansion of the graft to a variable size dependent upon conditions within the body passageway; permits tissue of an elongated section of a body passageway to be supported by an elongated graft; and provides the necessary flexibility to negotiate the bends and curves in tortuous body passageways, such as the vascular system.

BRIEF DESCRIPTION OF THE DRAWINGS

In the drawings:

FIG. 1A is a perspective view of an expandable intraluminal vascular graft, or prosthesis for a body passageway, having a first diameter which permits delivery of the graft, or prosthesis, into a body passageway;

FIG. 1B is a perspective view of the graft, or prosthesis, of FIG. 1A, in its expanded configuration when disposed within a body passageway;

FIG. 2 is a cross-sectional view of the prosthesis taken along line 2—2 of FIG. 1B;

FIG. 3 is a cross-sectional view of an apparatus for intraluminally reinforcing a body passageway, or for expanding the lumen of a body passageway, illustrating a prosthesis, or intraluminal vascular graft, in the configuration shown in FIG. 1A;

FIG. 4 is a cross-sectional view of the apparatus for intraluminally reinforcing a body passageway, or for expanding the lumen of a body passageway, with the graft, or prosthesis, in the configurations shown in FIG. 1B;

FIGS. 5 and 6 are perspective views of prostheses for a body passageway, with the grafts, or prostheses, having a coating thereon;

FIG. 7 is a perspective view of another embodiment of a graft or prosthesis in accordance with the present invention; and FIG. 8 is a perspective view of the graft of FIG. 7, wherein the graft has been bent or articulated.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

In FIGS. 1A and 1B, an expandable intraluminal vascular graft, or expandable prosthesis for a body passageway, 70 is illustrated. It should be understood that the terms "expandable intraluminal vascular graft" and "expandable prosthesis" are interchangeably used to some extent in describing the present invention, insofar as the methods, apparatus, and structures of the present invention may be utilized not only in connection with an expandable intraluminal vascular graft for expanding partially occluded segments of a blood vessel, or body passageway, but may also be utilized for many other purposes as an expandable prosthesis for many other types of body passageways. For example, expandable prostheses 70 may also be used for such purposes as: (1) supportive graft placement within blocked arteries opened by transluminal recanalization, but which are likely to collapse in the absence of an internal support; (2) similar use following catheter passage through mediastinal and other veins occluded by inoperable cancers; (3) reinforcement of catheter created intrahepatic communications between portal and hepatic veins in patients suffering from portal hypertension; (4) supportive graft placement of narrowing of the esophagus, the intestine, the ureters, the urethra; and (5) supportive graft reinforcement of reopened and previously obstructed bile ducts. Accordingly, use of the term "prosthesis" encompasses the foregoing usages within various types of body passageways, and the use of the term "intraluminal vascular graft" encompasses use for expanding the lumen of a body passageway. Further, in this regard, the term "body passageway" encompasses any duct within the human body, such as those previously described, as well as any vein, artery, or blood vessel within the human vascular system.

Still with reference to FIGS. 1A and 1B, the expandable intraluminal vascular graft, or prosthesis, 70 is shown to generally comprise a tubular member 71 having first and second ends 72, 73 and a wall surface 74 disposed between the first and second ends 72, 73. Tubular member 71 has a first diameter, d, which, to be hereinafter described in greater detail, permits intraluminal delivery of the tubular member 71 into a body passageway 80 having a lumen 81 (FIG. 3). With reference to FIG. 1B, upon the application from the interior of the tubular member 71 of a radially, outwardly extending force, to be hereinafter described in greater detail tubular member 71 has a second, expanded diameter, d', which second diameter d, is variable in size and dependent upon the amount of force applied to deform the tubular member 71.

Tubular member 71, may be any suitable material which is compatible with the human body and the bodily fluids (not shown) with which the vascular graft, or prosthesis, 70 may come into contact. Tubular member 71 must also be made of a material which has the requisite strength and elasticity characteristics to permit the tubular member 71 to be expanded and deformed from the configuration shown in FIG. 1A to the configuration shown illustrated in FIG. 1B and further to permit the tubular member 71 to retain its expanded and deformed configuration with the enlarged diameter d' shown in FIG. 1B and resist radial collapse. Suitable materials for the fabrication of tubular member 71 would include silver, tantalum, stainless steel, gold, titanium or any suitable plastic material having the requisite characteristics previously described.

Preferably, tubular member 71 is initially a thin-walled stainless steel tube having a uniform wall thickness, and a plurality of slots 82 are formed in the wall surface 74 of tubular member 71. As seen in FIG. 1A when tubular member 71 has the first diameter d, the slots 82 are disposed substantially parallel to the longitudinal axis of the tubular member 71. As seen in FIG. 1A, the slots 82 are preferably uniformly and circumferentially spaced from adjacent slots 82, as by connecting members 77, which connecting members 77 preferably have a length equal to the width of slots 82, as seen in FIG. 1A. Slots 82 are further uniformly spaced from adjacent slots 82 along the longitudinal axis of the tubular member 71, which spacing is preferably equal to the width of connecting members 77. Thus, the formation of slots 82 results in at least one elongate member 75 being formed between adjacent slots 82, elongate member 75 extending between the first and second ends, 72, 73 of tubular member 71, as seen in FIG. 1A.

Still with reference to FIG. 1A, each slot will have first and second ends with a connecting member 77 disposed at the first and second ends of slots 82. Preferably, the first and second ends of each slot 82 are disposed intermediate the first and second ends of adjacent slots 82 along the longitudinal axis of the tubular member 71. Thus, connecting members 77, which are disposed at the first and second ends of each slot 82, and between elongate members 75, will in turn be disposed intermediate the first and second ends of adjacent slots 82 along the longitudinal axis of the tubular member 71. Accordingly, slots 82 are preferably uniformly and circumferentially spaced from adjacent slots, and slots 82 adjacent to one another along the longitudinal axis of tubular member 71 are in a staggered relationship with one another. Alternating slots disposed about the circumference of tubular member 71 at both the first and second ends 72, 73 of tubular member 71 will only have a length equal to approximately one-half of the length of a complete slot 82, such half-slot 82 being bounded by members 78, 79, at both the first and second ends 72, 73 of tubular member 71. Although the graft, or prosthesis, 70 of FIGS. 1A and 1B is illustrated to have a length approximately equal to the length of two slots 82, it should be apparent that the length of the graft 70 could be made longer or shorter as desired.

The foregoing described construction of graft, or prosthesis, 70 permits graft, or prosthesis, 70 to be expanded uniformly, and outwardly, in a controlled manner into the configuration shown in FIG. 1B, upon the application of a suitable force from the interior of tubular member 71, as will be hereinafter described in greater detail. The expansion of tubular member 71 into the configuration shown in FIG. 1B is further uniform along the length of tubular member 71, not only because of the uniform spacing between slots 82, as previously described, but also because the thickness of the wall surface 74, or the thickness of connecting members 77, elongate members 75, and members 78, 79, is the same uniform thickness. As illustrated in FIG. 2, the uniform thickness of elongate member 75 is shown, and the preferred cross-sectional configuration of elongate member 75, connecting member 77, and members 78, 79, is illustrated, which configuration is rectangular. It should of course be understood by those skilled in the art, that the cross-sectional configuration of the foregoing components of graft, or prosthesis, 70 could also be square, rectangular, or other cross-sectional configurations. As will be hereinafter described in greater detail, it is preferable that the outer surface 74 of graft, or prosthesis, 70, which would be in contact with the body passageway 80 FIG. 4, should be relatively smooth.

With reference to FIG. 1B, it is seen that after the graft, or prosthesis 70, has been expanded and deformed into the configuration of FIG. 1B, the slots 82 will assume a substantially hexagonal configuration when the tubular member 71 has the second, expanded diameter, d', as shown in FIG. 1B. Such a hexagonal configuration will result when the slots 82 initially have a substantially rectangular configuration when the tubular member 71 has the first diameter, d, illustrated in FIG. 1A. It should be noted that were the width of slots 82 to be substantially reduced, whereby the length of connecting member 77 would approximate a single point intersection, the expansion of such a tubular member 71 would result in slots 82 assuming a configuration which would be substantially a parallelogram (not shown).

It should be noted that not only is tubular member 71 expanded from the configuration shown in FIG. 1A to achieve the configuration shown in FIG. 1B, but tubular member 71 is further "deformed" to achieve that configuration. By use of the term "deformed" is meant that the material from which graft, or prosthesis, 70 is manufactured is subjected to a force which is greater than the elastic limit of the material utilized to make tubular member 71. Accordingly, the force is sufficient to permanently bend elongate members 75 whereby segments of the elongate members 75 pivot about connecting members 77 and move in a circumferential direction as they pivot, whereby the diameter of the tubular member 71 increases from the first diameter, d, to the expanded diameter, d', of FIG. 1B. The force to be applied to expand tubular member 71, which is applied in the manner which will be hereinafter described in greater detail, must thus be sufficient to not only expand tubular member 71, but also to deform elongate member 75, in the manner previously described, whereby the portions of the elongate members 75 which pivot about the ends of connecting members 77 do not "spring back" and assume their configuration shown in FIG. 1A, but rather retain the configuration thereof in FIG. 1B. Once graft, or prosthesis, 70 has been expanded and deformed into the configuration shown in FIG. 1B, graft, or prosthesis 70, will serve to prevent a body passageway from collapsing as will be hereinafter described in greater detail. It should be noted that when tubular member 71 has the first diameter, d, shown in FIG. 1A, or after tubular member 71 has been expanded and deformed into the second, expanded diameter, d', of FIG. 1B, tubular member 71 does not exert any outward, radial force, in that tubular member 71 is not a "spring-like" or "self-expanding member", which would tend to exert an outwardly radial force.

With reference now to FIGS. 3 and 4, apparatus of the present invention will be described in greater detail. Once again, it should be understood that the apparatus of the present invention is useful not only for expanding the lumen of a body passageway, such as an artery, vein, or blood vessel of the human vascular system, but are also useful to perform the previously described procedures to intraluminally reinforce other body passageways or ducts, as previously described. Still with reference to FIGS. 3 and 4, an expandable intraluminal vascular graft, or prosthesis, 70, of the type described in connection with FIGS. 1A and 1B, is disposed or mounted upon a catheter 83. Catheter 83 has an expandable, inflatable portion 84 associated therewith. Catheter 83 may include means for mounting and retaining 85 the expandable intraluminal vascular graft, of prosthesis, 70 on the expandable, inflatable portion 84 of catheter 83. The mounting and retaining means 85 could comprise retainer ring members 86 disposed on the catheter 83 adjacent the expandable inflatable portion 84 of catheter 83; and a retainer ring member 86 is disposed adjacent each end 72, 73 of the expandable intraluminal vascular graft, or prosthesis, 70. As seen in FIG. 3, retainer ring members could be formed integral with catheter 83, and the retainer ring member 86 adjacent the leading tip 87 of catheter 83 slopes upwardly and away from catheter tip 87 in order to protect and retain graft or prosthesis, 70 as it is inserted into the lumen 81 of body passageway 80, as to be hereinafter described in greater detail. The remaining retainer ring member 86 as shown in FIG. 3, slopes downwardly away from tip 87 of catheter 83, to insure easy removal of catheter 83 from body passageway 80. After expandable intraluminal graft, or prosthesis, 70 has been disposed upon catheter 83, in the manner previously described, the graft, or prosthesis, 70 and catheter 83 are inserted within a body passageway 80 by catheterization of the body passageway 80 in a conventional manner.

In a conventional manner, the catheter 83 and graft, or prosthesis, 70 are delivered to the desired location within the body passageway 80, whereat it is desired to expand the lumen 81 of body passageway 80 via intraluminal graft 70, or where it is desired to implant prosthesis 70. Fluoroscopy, and/or other conventional techniques may be utilized to insure that the catheter 83 and graft, or prosthesis, 70 are delivered to the desired location within the body passageway. Prosthesis, or graft, 70 is then controllably expanded and deformed by controllably expanding the expandable, inflatable portion 84 of catheter 83, whereby the prosthesis, or graft, 70 is expanded and deformed radially, outwardly into contact with the body passageway 80, as shown in FIG. 4. In this regard, the expandable, inflatable portion of catheter 83 may be a conventional angioplasty balloon 88. After the desired expansion and deformation of prosthesis, or graft, 70 has been accomplished, angioplasty balloon 88 may be collapsed, or deflated, and the catheter 83 may be removed in a conventional manner from body passageway 80. If desired, as seen in FIG. 3, catheter 83, having graft or prosthesis, 70 disposed thereon, may be initially encased in a conventional Teflon sheath 89, or a sheath 89 made of another suitable material, which is pulled away from prosthesis, or graft, 70, prior to expansion of the the prosthesis, or graft, 70.

Still with reference to FIGS. 3 and 4, it should be noted that tubular member 71 of prosthesis, or graft, 70 initially has the first predetermined, collapsed diameter, d, as described in connection with FIG. 1A, in order to permit the insertion of the tubular member, 71 into the body passageway 80 as previously described. When it is desired to implant prosthesis 70 within a body passageway 80 for the purposes previously described, the prosthesis 70 is, controllably expanded and deformed to the second diameter, d', and the second, expanded diameter, d,, is variable and determined by the internal diameter of the body passageway 80, as shown in FIG. 4, and by the amount of expansion of the inflatable portion 84 of catheter 83. Accordingly, the expanded and deformed prosthesis 70, upon deflation of angioplasty balloon 88 will not be able to migrate from the desired location within the body passageway 80, nor will the expansion of the prosthesis 70 be likely to cause a rupture of the body passageway 80. Furthermore, insofar as prosthesis, or graft, 70 is not a "spring-like" or "self-expanding member", the prosthesis is not consistently applying an outward, radial force against the interior surface of body passageway 80, in excess of that required to resist radial collapse of the body passageway 80. Thus, erosion of the interior surface, or intima, of the artery or body passageway is prevented.

When it is desired to use expandable intraluminal graft 70 to expand the lumen 81 of a body passageway 80 having an area of stenosis, the expansion of intraluminal vascular graft 70 by angioplasty balloon 88, allows controlled dilation of the stenotic area and, at the same time controlled expansion and deformation of the vascular graft 70, whereby vascular graft 70 prevents the body passageway 80 from collapsing and decreasing the size of the previously expanded lumen 81. Once again, the second, expanded diameter d' of intraluminal vascular graft 70, as shown in FIG. 4, is variable and determined by the desired expanded internal diameter of body passageway 80. Thus, the expandable intraluminal graft 70 will not migrate away from the desired location within the body passageway 80 upon deflation of angioplasty balloon 88, nor will the expansion of intraluminal graft 70 likely cause a rupture of body passageway 80, nor any erosion as previously described. Further, should an intimal flap, or fissure, be formed in body passageway 80 at the location of graft 70, graft 70 will insure that such an intimal flap will not be able to fold inwardly into body passageway 80, nor tear loose and flow through body passageway 80. In the situation of utilizing graft 70 in the manner previously described to expand the lumen of a portion of a critical body passageway, such as the left main coronary artery, it is believed that the intimal flap will be unable to occlude the left main coronary artery of the heart and cause the death of the patient.

Because it is only necessary to inflate angioplasty balloon 88 one time in order to expand and deform graft 70, it is believed that a greater amount of endothelium, or inner layer of the intima, or inner surface of the body passageway, will be preserved, insofar as the extent of endothelial denudation during transluminal angioplasty is proportional to the balloon inflation time. Further, in theory, the amount of preserved endothelium should be large because in the expanded configuration of graft 70, potentially 80% of the endothelium is exposed through the openings or expanded slots 82 of graft 70. It is further believed that intact patches of endothelium within expanded slots 82 of graft 70 may result in a rapid, multicentric endothelialization pattern as shown by experimental studies.

With reference now to FIGS. 5 and 6, prostheses, or grafts, 70 of the type previously described in connection with FIGS. 1A and 1B are shown, and the tubular members 71 of grafts, or prostheses, 70 have a biologically inert or biologically compatible coating 90 placed upon wall surfaces 74 of tubular shaped members 71. Examples of a suitable biologically inert coating would be porous polyurethane, Teflon~, or other conventional biologically inert plastic materials. The coating 90 should be thin and highly elastic so as not to interfere with the desired expansion and deformation of prosthesis, or graft, 70. Coating 90 may be further provided with a means for anchoring 91 (FIG. 6) the tubular member 71 to the body passageway 80. Anchoring means 91 may be comprised of a plurality of radially, outwardly extending projections 92 formed on the coating 90. As seen in FIG. 6, the radially outwardly extending projections 92 could comprise a plurality of ridges 93, or other types of radially, outwardly extending projections. Further, it may be desirable to have a plurality of openings 94 formed in coating 90, as shown in FIG. 5, whereby the fluid contained in body passageway 80 can be in direct contact with the dilated, or expanded, body passageway area. Examples of biologically compatible coatings 90 would include coatings made of absorbable polymers such as those used to manufacture absorbable sutures. Such absorbable polymers include polyglycoides, polylactides, and copolymers thereof. Such absorbable polymers could also contain various types of drugs, whereby as the coating 90 is absorbed, or dissolves, the drug would be slowly released into the body passageway 80.

Turning now to FIGS. 7 and 8, an expandable intraluminal vascular graft, or prosthesis, 70' is shown for implantation in curved body passageways 80, or for use in the elongated sections of body passageway 80, when a prosthesis or a graft, 70' is required which is longer than the graft, or prosthesis, 70 of FIG. 1A. Identical reference numerals are used throughout FIGS. 7 and 8 for elements which are the same in design, construction, and operation, as those previously described in connection with FIGS. 1A-6, and primed reference numerals are used for elements which are similar in construction, design, and operation, as those previously described in connection with 1A-6.

As seen in FIG. 7, graft, or prosthesis, 70' generally includes a plurality of prostheses, or grafts, 70 as described previously in connection with FIGS. 1A, 1B, and 2. Disposed between adjacent tubular members, 71, or adjacent grafts, or prostheses, 70, is a single connector member 100 to flexibly connect adjacent tubular members 71 or grafts, or prostheses, 70. Connector members 100 are preferably formed of the same material as grafts 70, as previously described, and connector members 100 may be formed integrally between adjacent grafts 70, or tubular members 71, as shown in FIG. 7. The cross-sectional configuration of connector members 100, along the longitudinal axis of graft, or prosthesis, 70', is the same, in that connector members 100 have the same uniform wall thickness of elongate members 75 and thus form a thin-walled, elongate bar member 101 which is coplanar with adjacent tubular members 71. Of course, it should be readily apparent to one of ordinary skill in the art, that the thickness of connector members 100 could alternatively be smaller than elongate member 75; however, it is pre ferable that the outer circumferential surface 102 of connector members 100 lies in the same plane formed by the wall surfaces 74 of grafts, or prostheses, 70, as seen in FIG. 7.

Still with reference to FIGS. 7-8, it should be noted that although graft, or prosthesis, 70' is illustrated as including three grafts, or prostheses, 70 flexibly connected to one another by connector members 100, as few as two grafts 70 could be connected to form graft, or prosthesis, 70'. Furthermore, many grafts 70 could be flexibly connected by connector members 100 as are desired to form graft, or prosthesis, 70'. Preferably, the length of each graft, or prosthesis, 70 is approximately the length of two slots 82; however, the length of each graft 70 could be approximately equal to the length of two or more slots 82. When three or more grafts 70 are flexibly connected by connector members 100, as shown in FIGS. 7 and 8, preferably a first connector member 100 is disposed between the second end 73 of a first tubular member 70A and the first end 72 of a second tubular member 70B. A second connector member 100 is then disposed between the second end 73 of the second tubular member 70B and the first end 72 of a third tubular member 70C. The first and second connector members 100, as shown in FIGS. 7 and 8, may be angularly offset from one another with respect to the longitudinal axis of the tubular members 70 to permit the requisite flexibility between the interconnected grafts, or prostheses, 70.

The delivery and expansion of graft, or prosthesis, 70' is the same as that previously described in connection with FIGS. 1A, 1B, and 3-4. The length of the expandable, inflatable portion 84 of catheter 83 would be sized to conform with the length of the graft, or prosthesis, 70', as should be readily apparent to one of ordinary skill in the art. Except for the length of the expandable, inflatable portion 84, catheter 83, the method of delivery of graft, or prosthesis, 70' and its subsequent, controllable expansion and deformation are the same as previously described. As seen in FIG. 8, the prosthesis 70' is illustrated in the configuration it would assume when being delivered to the desired location within the body passageway 80, and the graft, or prosthesis, 70' is disposed upon catheter 83 and is passing through a curved portion of body passageway 80, such as an arterial bend. Because of the disposition of flexible connector members 100 between adjacent tubular members 71, or grafts, or prostheses, 70, graft, or prosthesis, 70' is able to flexibly bend, or articulate, with respect to the longitudinal axis of graft, or prosthesis, 70', so as to be able to negotiate the curves or bends found in body passageways 80. It should be noted that connector members 100 permit the bending, or articulation of adjacent tubular members 71 in any direction about the longitudinal axis of graft, or prosthesis, 70'. When graft, or prosthesis, 70' is in its expanded, and deformed configuration, tubular members 71 of graft, or prosthesis, 70', will assume the configuration shown in FIG. 1B.

It is to be understood that the invention is not to be limited to the exact details of construction, operation, exact materials, or embodiments shown and described, as obvious modifications and equivalents will be apparent to one skilled in the art. Accordingly, the invention is therefore to be limited only by the scope of the appended claims.

I claim:

1. An expandable intraluminal vascular graft, comprising:
   a plurality of thin-walled tubular members, each having first and second ends and a wall surface disposed between the first and second ends, the wall surface having a substantially uniform thickness and a plurality of slots formed therein, the slots being disposed substantially parallel to the longitudinal axis of each tubular member;
   only one connector member being disposed between adjacent tubular members to flexibly connect adjacent tubular members, the connector member being disposed in a substantially parallel relationship with respect to the longitudinal axis of the tubular members and coplanar with each tubular member.
   each tubular member having a first diameter which permits intraluminal delivery of the tubular members into a body passageway having a lumen; and
   the tubular members having a second, expanded and deformed diameter, upon the application from the interior of the tubular members of a radially, outwardly extending force, which second diameter is variable and dependent upon the amount of force applied to the tubular members, whereby the tubular members may be expanded and deformed to expand the lumen of the body passageway.

2. The expandable intraluminal graft of claim 1, wherein the connector member is a thin-walled, elongate bar member, coplanar with adjacent tubular members.

3. The expandable intraluminal graft of claim 1, wherein a first connector member is disposed between the second end of a first tubular member and the first end of a second tubular member; a second connector member is disposed between the second end of the second tubular member and the first end of a third tubular member, the first and second connector members being angularly offset from one another and with respect to the longitudinal axes of the tubular members they interconnect.

4. An expandable prosthesis for a body passageway, comprising:
   a plurality of thin-walled tubular members, each having first and second ends and a wall surface disposed between the first and second ends, the wall surface having a substantially uniform thickness and a plurality of slots formed therein, the slots being disposed substantially parallel to the longitudinal axis of each tubular member;
   only one single connector member being disposed between adjacent tubular members to flexibly connect adjacent tubular members, the connector member being disposed in a substantially parallel relationship with respect to the longitudinal axis of the tubular members and coplanar with each tubular member;
   each tubular member having a first diameter which permits intraluminal delivery of the tubular members into a body passageway having a lumen; and
   the tubular members having a second, expanded and deformed diameter, upon the application from the interior of the tubular members, of a radially, outwardly extending force, which second diameter is variable and dependent upon the amount of force applied to the tubular member, whereby the tubular member may be expanded and deformed to expand the lumen of the body passageway.

5. The expandable prosthesis of claim 4, wherein the connector member is a thin-walled, elongate bar member, coplanar with adjacent tubular members.

6. The expandable prosthesis of claim 4, wherein a first connector member is disposed between the second end of a first tubular member and the first end of a second tubular member; a second connector member is disposed between the second end of the second tubular member and the first end of a third tubular member, the first and second connector members being angularly offset from one another and with respect to the longitudinal axes of the tubular members they interconnect.

* * * * *

(12) EX PARTE REEXAMINATION CERTIFICATE (5538th)
United States Patent
Schatz

(10) Number: US 5,195,984 C1
(45) Certificate Issued: Oct. 3, 2006

(54) EXPANDABLE INTRALUMINAL GRAFT

(75) Inventor: Richard A. Schatz, Paradise Valley, AZ (US)

(73) Assignee: Cordis Corporation, Miami, FL (US)

Reexamination Request:
No. 90/007,628, Jul. 13, 2005

Reexamination Certificate for:
Patent No.: 5,195,984
Issued: Mar. 23, 1993
Appl. No.: 07/657,296
Filed: Feb. 19, 1991

Related U.S. Application Data

(63) Continuation of application No. 07/253,115, filed on Oct. 4, 1988, now abandoned.

(51) Int. Cl.
*A61M 29/00* (2006.01)
*A61F 2/06* (2006.01)

(52) U.S. Cl. .................. 623/1.2; 623/1.16; 604/103.05; 604/104; 606/193; 606/194; 606/195

(58) Field of Classification Search ................. 606/198; 623/1.1–1.54, 23.7
See application file for complete search history.

(56) References Cited

U.S. PATENT DOCUMENTS

| | | |
|---|---|---|
| 861,659 A | 7/1907 | Johnston |
| 3,279,996 A | 10/1966 | Long et al. |
| 3,526,005 A | 9/1970 | Bokros |
| 3,599,641 A | 8/1971 | Sheridan |
| 3,657,744 A | 4/1972 | Ersek |
| 3,744,596 A | 7/1973 | Sander |
| 3,932,627 A | 1/1976 | Margraf |
| 3,948,254 A | 4/1976 | Zaffaroni |
| 3,952,334 A | 4/1976 | Bokros et al. |
| 3,968,800 A | 7/1976 | Vilasi |
| 4,069,307 A | 1/1978 | Higuchi et al. |
| 4,076,285 A | 2/1978 | Martinez |
| 4,292,965 A | 10/1981 | Nash |
| 4,299,226 A | 11/1981 | Banka |
| 4,300,244 A | 11/1981 | Bokros |
| 4,312,920 A | 1/1982 | Pierce et al. |

(Continued)

FOREIGN PATENT DOCUMENTS

| | | |
|---|---|---|
| EP | 0 145 166 | 10/1984 |
| EP | 0 183 372 | 10/1985 |
| EP | 1 177 330 | 10/1985 |
| EP | 0 221 570 | 11/1986 |
| EP | 0 421 729 | 4/1991 |
| GB | 1 205 743 | 10/1967 |
| GB | 2 135 585 A | 4/1983 |
| SU | 660689 | 11/1977 |
| SU | 1457921 | 2/1989 |
| WO | WO 89/03232 | 4/1989 |

OTHER PUBLICATIONS

Trial Transcript from Nov. 6, 2000 at 185–90 and 235–36 (Attorneys' opening remarks regarding '984 patent).

Trial Transcript from Nov. 7, 2000 at 274–301, 307–315, 320–28 and 332 (Cordis expert testimony regarding the Palmaz–Schatz stent); 370–379, 480–496 (J. Palmaz testimony regarding the Palmaz–Schatz stent, the '984 patent and the connected z–stent art).

Trial Transcript from Nov. 8, 2000 at 547–63, 657–63, 674–722, 782–85 (Cordis expert testimony regarding the Palmaz–Schatz stent, the '984 patent and the connected z–stent art).

(Continued)

*Primary Examiner*—David O. Reip

(57) ABSTRACT

A plurality of expandable and deformable intraluminal vascular grafts are expanded within a blood vessel by an angioplasty balloon associated with a catheter to dilate and expand the lumen of a blood vessel. The grafts may be thin-walled tubular members having a plurality of slots disposed substantially parallel to the longitudinal axis of the tubular members, and adjacent grafts are flexibly connected by a single connector member disposed substantially parallel to the longitudinal axis of the tubular members.

U.S. PATENT DOCUMENTS

| | | |
|---|---|---|
| 4,321,711 A | 3/1982 | Mano |
| 4,323,071 A | 4/1982 | Simpson et al. |
| 4,390,599 A | 6/1983 | Broyles |
| 4,503,569 A | 3/1985 | Dotter |
| 4,512,338 A | 4/1985 | Balko et al. |
| 4,550,447 A | 11/1985 | Seiler, Jr. et al. |
| 4,553,545 A | 11/1985 | Maass et al. |
| 4,560,374 A | 12/1985 | Hammerslag |
| 4,562,596 A | 1/1986 | Kronberg |
| 4,565,740 A | 1/1986 | Golander et al. |
| 4,580,568 A | 4/1986 | Gianturco |
| 4,613,665 A | 9/1986 | Larm |
| 4,642,111 A | 2/1987 | Sakamoto et al. |
| 4,655,771 A | 4/1987 | Wallsten |
| 4,656,083 A | 4/1987 | Hoffman et al. |
| 4,676,241 A | 6/1987 | Webb et al. |
| 4,678,466 A | 7/1987 | Rosenwald |
| 4,687,482 A | 8/1987 | Hanson |
| 4,689,046 A | 8/1987 | Bokros |
| 4,731,054 A | 3/1988 | Billeter et al. |
| 4,733,665 A | 3/1988 | Palmaz |
| 4,739,762 A | 4/1988 | Palmaz |
| 4,740,207 A | 4/1988 | Kreamer |
| 4,753,652 A | 6/1988 | Langer et al. |
| 4,760,849 A | 8/1988 | Kropf |
| 4,768,507 A | 9/1988 | Fischell et al. |
| 4,776,337 A | 10/1988 | Palmaz |
| 4,787,899 A | 11/1988 | Lazarus |
| 4,800,882 A | 1/1989 | Gianturco |
| 4,810,784 A | 3/1989 | Larm |
| 4,856,516 A | 8/1989 | Hillstead |
| 4,872,867 A | 10/1989 | Joh |
| 4,886,062 A | 12/1989 | Wiktor |
| 4,916,193 A | 4/1990 | Tang |
| 4,969,458 A | 11/1990 | Wiktor |
| 4,994,298 A | 2/1991 | Yasuda |
| 4,998,923 A | 3/1991 | Samson et al. |
| 5,019,090 A | 5/1991 | Pinchuk |
| 5,019,096 A | 5/1991 | Fox et al. |
| 5,029,877 A | 7/1991 | Fedeli et al. |
| 5,034,265 A | 7/1991 | Hoffman et al. |
| 5,049,403 A | 9/1991 | Larm et al. |
| 5,053,048 A | 10/1991 | Pinchuk |
| 5,059,166 A | 10/1991 | Fischell et al. |
| 5,102,417 A | 4/1992 | Palmaz |
| 5,133,732 A | 7/1992 | Wiktor |
| 5,135,536 A | 8/1992 | Hillstead |
| 5,182,317 A | 1/1993 | Winters et al. |
| 5,213,898 A | 5/1993 | Larm et al. |
| 5,226,913 A | 7/1993 | Pinchuk |
| 5,262,451 A | 11/1993 | Winters et al. |
| 5,338,770 A | 8/1994 | Winters et al. |
| 5,383,928 A | 1/1995 | Scott et al. |
| 5,474,563 A | 12/1995 | Myler |
| 5,512,055 A | 4/1996 | Domb et al. |
| 5,545,208 A | 8/1996 | Wolff et al. |
| 5,591,227 A | 1/1997 | Dinh et al. |
| 5,624,411 A | 4/1997 | Tuch |
| 5,877,224 A | 3/1999 | Brocchini et al. |
| 6,120,536 A | 9/2000 | Ding et al. |

OTHER PUBLICATIONS

Trial Transcript from Nov. 9, 2000 at 819–23, 921 (Cordis expert testimony regarding the '984 patent); 926–941. (R. Croce testimony re Palmaz–Schatz stent); 1033–1053. (R. Schatz testimony).

Trial Transcript from Nov. 13, 2000 at 1086–1134. (R. Schatz testimony); 1275–1305 (Cordis expert testimony regarding the '984 patent).

Trial Transcript from Nov. 14, 2000 at 1390–1404, 1448–1454, 1486–1500 (Cordis expert testimony regarding the '984 patent).

Trial Transcript from Nov. 15, 2000 at 1686–87, 1724–42, 1828–34, 1850–54, 1887–92 (AVE expert testimony regarding the '984 patent).

Trial Transcript from Nov. 16, 2000 at 2077–198 (AVE expert testimony regarding the alleged obviousness of the '984 patent).

Trial Transcript from Nov. 17, 2000 at 2331–34 (jury instructions as to the meaning of the limitations of the claims of the '984 patent).

Trial Transcript from Nov. 20, 2000 at 2441–48, 2499–2500, 2546–50, 2552–56 (Attorneys' closing arguments regarding the '984 patent).

Trial Transcript from Nov. 21, 2000 at 2592–94 (reading of jury verdict).

Trial Transcript from Dec. 18, 2000 at 2750–95 (Cordis expert testimony regarding the Palmaz–Schatz stent during the damages phase).

Trial Transcript from Dec. 20, 2000 at 3421–88 (AVE expert testimony regarding the Palmaz–Schatz stent during the damages phase).

Jury verdict, dated Nov. 21, 2000.

District Court decisions on post–trial motions (194 F. Supp. 2d 323).

Court of Appeal for the Federal Circuit decision (339 F.3d 1352).

Trial Transcript from Mar. 4, 2005 at 133–135, 171–173 and 192–96 (Attorney's opening remarks regarding '984 validity).

Trial Transcript from Mar. 7, 2005 at 275–311 (Cordis expert testimony regarding the Palmaz–Schatz stent); 342–46, 353–59, 416–425 (J. Palmaz testimony regarding the Palmaz–Schatz stent, the '984 patent and the connected z–stent art); 430–449, 452–58, 462–492 (R. Croce testimony regarding the Palmaz–Schatz stent); 500–507 (Cordis expert testimony regarding the '984 patent).

Trial Transcript from Mar, 8, 2005 at 609 (Cordis expert testimony regarding the '984 patent); 628–73, 724–740, 773, 801–839 (Cordis expert testimony regarding the '984 patent, the prior art and the Palmaz–Schatz stent).

Trial Transcript from Mar. 9, 2005 at 936–49, 968–69 (Cordis expert testimony regarding the '984 patent, the prior art and the Palmaz–Schatz stent).

Trial Transcript from Mar. 10, 2005 at 1427–74, 178–1509, 1514–23 (AVE expert testimony regarding the alleged obviousness of the '984 patent); 1566–93 (AVE expert testimony regarding Palmaz–Schatz stent); 1634–49 (R. Schatz testimony).

Trial Transcript from Mar. 11, 2005 at 1846–47, 1891–1900, 1919 (Attorneys' closing arguments regarding '984 obviousness).

Trial Transcript from Mar. 14, 2005 at 1964–67 (reading of jury verdict).

Jury verdict dated Mar. 14, 2005.

Medtronic Vascular Inc.'s Opening Brief in Support of Its Motion for Judgment As A Infringement Claim dated Apr. 19, 2005.

Medtronic Vascular Inc.'s Opening Brief in Support of Its Motion for a New Trial dated Apr. 19, 2005.

D.I. 1407, Cordis' Combined Answering Brief In Opposition to AVE's Motion for JMOL on Infringement of the Palmaz '762 and Schatz '984 Patents and Its Motion for a New Trial dated May 5, 2005.

D.I. 1414, Medtronic Vascular Inc.'s Combined Reply Brief In Support of Its Motion for Judgment as a Matter of Law on Cordis Corp.'s Patent Infringement Claims and Its Motion for a New Trial.

Trial Transcript from Feb. 8, 2001 at 372–412, 449–469 (B. Tobor testimony regarding the prosecution of the '417, '984 and '332 patents); 510–13 (J. Milnamow testimony regarding the prosecution of the '332 patent); 558–604 (J. Palmaz testimony regarding the prosecution of the '417, '984 and '332 patents and the prior art).

Trial Transcript from Feb. 9, 2001 at 637–45, 662–672, 682–85 (J. Palmaz testimony regarding the prior art); 699–742 (R. Schatz testimony); 769–770, 790–95 (Cordis expert testimony regarding prior art).

D.I. 1067, Medtronic AVE, Inc.'s Post–Trial Brief Relating to the Unenforceability of the '762 and '984 Patents Due to Inequitable Conduct.

D.I. 1077, Cordis' Combined Answering Brief in Opposition to AVE's BSC's Post–Hearing Briefs on Alleged Inequitable Conduct Concerning the '762, '984 and '332 Patents.

D.I. 1089, Reply Brief In Support of Medtronic AVE, Inc.'s Contention that the '762 and '984 Patents are Unenforceable Due to Inequitable Conduct dated May 7, 2001.

C.A. No. 00–886–SLR, Answer and Counterclaims of Def. Medtronic AVE, Inc. To First Amended Complaint of Plaintiff Cordis Corp.

BSC's Opening Post–Trial Brief in Support of Its Defense That the Patents in Suit Are Unenforceable, dated Mar. 16, 2001.

Reply Brief in Support of BSC's Defense That the Patents in Suit Are Unenforceable, dated May 7, 2001.

Court's Decision on allegations of inequitable conduct (194 F. Supp. 2d 323).

Trial Transcript from Nov. 21, 2000 at 155–57 and 180–84 (Attorneys' opening remarks regarding '332 patent).

Trial Transcript from Nov. 27, 2000 at 227–51, 260–300 (Cordis expert testimony regarding the Palmaz–Schatz stent); 343–60, 363–67, 424–33 (J. Palmaz testimony regarding the Palmaz–Schatz stent and the '332 patent).

Trial Transcript from Nov. 28, 2000 at 649–71.

Trial Transcript from Nov. 29, 2000 at 791–816, 859–870, 953–62 (Cordis expert testimony regarding the '332 patent and the Palmaz–Schatz stent).

Trial Transcript from Nov. 30, 2000 at 1018 (Cordis expert testimony regarding the '332 patent); 1062–80, 1108–1111 (R. Croce testimony regarding the Palmaz–Schatz stent); 1169–70, 1205–17, 1236–45 (Cordis expert testimony regarding the '332 patent).

Trial Transcript from Dec. 1, 2000 at 1352–54 (Cordis expert testimony regarding the '332 patent); 1364–1442 (R. Schatz testimony); 1493–1508, 1552–69 (BSC expert testimony regarding the '332 patent and the Palmaz–Schatz stent).

Trial Transcript from Dec. 4, 2000 at 1602–12, 1638–51, 1713–14, 1730–61, 1811–14, 1823–36 (BSC expert testimony regarding the alleged obviousness of the '332 patent, the prior art and the Palmaz–Schatz stent).

Trial Transcript from Dec. 6, 2000 at 2318–27, 2342–58 (BSC expert testimony regarding the '332 patent).

Trial Transcript from Dec. 7, 2000 at 2549–52 (Cordis expert testimony regarding the '332 patent); 2575–2579, 2591–92, 2630–31, 2649, 2669–71, 2684–85, 2688, 2708–10, 2725–27 (Attorney closing argument regarding '332 patent); 2742–46 (jury instructions as to the meaning of the limitations of the claims of the '332 patent).

Trial Transcript from Dec. 11, 2000 at 2817–22 (reading of jury verdict).

Jury verdict, dated Dec. 11, 2000.

District Court decisions on post–trial motions (194 F. Supp. 2d 323).

D.I. 699, Motion by Defendant BSC and Scimed Life Systems, Inc. For Summary Judgment of Invalidity of U.S. Pat. No. 5,902,332 dated Apr. 4, 2000.

D.I.896, Order Denying Motion for Summary Judgment of Invalidity and Unenforceability of Claims 1, 3, and 5 of the U.S. Pat. No. 5,902,332 Denying {699–1} Motion for Summary Judgment of Invalidity of U.S. Pat. No. 5,902,332 dated Oct. 12, 2000.

Wright et al., Percutaneous Endovascular Stent: An Experimental Study (Abstract), RSNA Meeting (Nov. 28, 1984).

Hearing Transcript from Feb. 10, 1998 at 122–32, 146–80 (Attorneys' opening remarks regarding '417 patent); 180–312 (R. Schatz testimony) [Portions of This Transcript Have Been Removed as Confidential].

Hearing Transcript from Feb. 11, 1998 at 427–575, 577–651 (Cordis expert testimony regarding the '417 patent, the prior art and the Palmaz–Schatz stent).

Hearing Transcript from Feb. 12, 1998 at 660–772 (Cordis expert testimony regarding the '417 patent, the Palmaz–Schatz stent and the prior art). [Portions of This Transcript Have Been Removed As Confidential].

Hearing Transcript from Feb. 13, 1998 at 1121–1261 (Guidant expert testimony regarding the alleged obviousness of the '417 patent, the prior art and the Palmaz–Schatz stent). [Portions of This Transcript Have Been Removed as Confidential].

Order by J. Robinson denying Cordis' Motion for a Preliminary Injunction Against ACS dated Jul. 17, 1998.

ACS, Inc.'s and Guidant Corp.'s Opening Brief in Support of Their Motion for Summary Judgment of Invalidity of U.S. Pat. No. 5,102,417 dated Aug. 27, 1998.

Plaintiffs' Answering Brief in Opposition to ACS' and BSC's Motion for Summary Judgment on Obviousness dated Sep. 24, 1998.

Order dated Mar. 31, 2000.

Schatz Deposition Testimony; May 15, 1996: 79–83, 89–92, 105–107 and 153–161.

Schatz Deposition Testimony; May 16, 1996: 555–564, 569–572.

Schatz Deposition Testimony; Jan. 18, 1998: 67–73, 108–110.

Schatz Deposition Testimony; Jul. 14, 1998: 69–77, 108–112, 119–123.

Schatz Deposition Testimony; Jul. 12, 1999: 88–91, 132–135, 144–149, 218–223, 231–242.

Schatz Deposition Testimony; Jul. 13, 1999: 251–334, 339–345, 374–416.

Schatz Deposition Testimony; Jul. 14, 1999: 454–550.

Schatz Deposition Testimony; Jul. 15, 1999: 560–614.

Schatz Deposition Testimony; Dec. 2, 1999: 906–911, 928–942, 945–963, 976–978, 1029–1034, 1038–1042.

Palmaz Deposition Testimony, Nov. 5, 1991: 160–172.

Palmaz Deposition Testimony, Feb. 5, 1995: 710–727.

Palmaz Deposition Testimony, Jul. 16, 1998: 55–56; 81–82.
Palmaz Deposition Testimony, Jul. 28, 1999: 560–568, 570–579.
Palmaz Deposition Testimony, Jul. 29, 1999: 778–785.
Palmaz Deposition Testimony, Aug. 31, 1999: 1403–1452.
Palmaz Deposition Testimony, Sep. 2, 1999: 1953–1960.
Palmaz Deposition Testimony, Oct. 14, 1999: 2201–2209; 2275–2342; 2371–2411.
Palmaz Deposition Testimony, Oct. 15, 1999: 2424–2497; 2508–2589.
Palmaz Deposition Testimony, Oct. 16, 1999: 2853–2860.
Tobor Deposition Testimony, Jun. 17, 1999: 837–958.
Tobor Deposition Testimony, Jun. 18, 1999: 1095–1184.
Tobor Deposition Testimony, Dec. 1, 1999: 1217–1371.
Tobor Deposition Testimony, Dec. 2, 1999: 1398–1414; 1444–1508; 1532–1548.
Tobor Deposition Testimony, Dec. 3, 1999: 1652–1653; 1662–1672; 1683–1694.
Kula Deposition Testimony, Apr. 20, 1999: 268–169.
Kula Deposition Testimony, Nov. 16, 1999: 660–675; 680–694; 7–8–755; 774–821.
Kula Deposition Testimony, Nov. 18, 1999; 176–223.
Expert Report of Dr. Rodney S. Badger on Behalf of Medtronic AVE, Inc. (Jan. 31, 2000).
Expert Report of Dr. Joseph Bonn on Behalf of Medtronic AVE, Inc. (Jan. 31, 2000).
Deposition of Dr. Joseph Bonn dated Mar. 14, 2000.
Rebuttal Expert Report of Nigel Buller, B.Sc., M.B., F.R.C.P. (Mar. 2000).
Second Supplemental Rebuttal Expert Report of Nigel Buller, B.Sc., M.B., F.R.C.P. (Aug. 17, 2004).
Rebuttal Expert Report of John M. Collins, PH.D. (Feb. 2000).
Expert Report of David C. Cumberland, M.D. (Jan. 24, 2000).
Expert Report of John T. Goolkasian (Feb. 2000).
Deposition of Richard R. Heuser, M.D. (Sep. 7, 2004).
Deposition of Henry R. Piehler (Sep. 10, 2004).
Deposition of Ronald J. Solar (Mar. 22, 2000).
Deposition of Ronald J. Solar (Mar. 23, 2000).
Deposition of Ronald J. Solar (Apr. 12, 2000).
Expert Report of Dr. Arina Van Breda on Behalf of Medtronic AVE, Inc. (Jan. 31, 2000).
Deposition of Arina Van Breda (Mar. 24, 2000.
Deposition of Arina Van Breda (Aug. 21, 2004).
Expert Report of John F. Witherspoon (Jan. 24, 2000).
Supplemental Expert Report of John F. Witherspoon (Oct. 27, 2000).
Deposition of John F. Witherspoon (Mar. 8, 2000).
Palmaz et al., Article: Normal and Stenotic Renal Arteries: Experimental Balloon Expandable Intraluminal Stenting, Radiology, Sep. 1987. (AVE 84).
Julio C. Palmaz, Article: "Expandable vascular endoprosthesis." (AVE 132).
Duprat et. al., Article: Flexible Balloon–Expandable Stent for Small Vessels Duprat et. al. Radiology, vol. 162, pp. 276–278, 1987. (AVE 134).
Coons et. al., Article: "Large–Bore, Long Biliary Endoprosthesis (Biliary Stents) for Improved Drainage," Radiology, vol. 148, pp. 89–94, 1983. (AVE 143).
Honickman et al., Article: "Malpositioned Biliary Endoprosthesis, Technical Developments And Instrumentation," vol. 144, No. 2., 1982. (AVE 144).

Harries–Jones, et al., Article: "Repositioning of Biliary Endoprosthesis with Gruntzig Balloon Catheters," AJR, vol. 138, pp. 771–772, 1982. (AVE 153).
Charnsangavej et al., Article "Stenosis of the Vena Cava: Preliminary Assessment of Treatment with Expandable Metallic Stents," Radiology, vol. 161, pp. 295–298, 1986. (AVE 359).
Article "Tracheobronchial Tree: Expandable Metallic Stents Used in Experimental and Clinical Applications," Radiology, vol. 158, pp. 309–312, 1986. (AVE 364).
T. Yoshioka, et al., AJR Article: "Self–Expanding Endovascular Graft: An Experimental Study in Dogs", vol. 151, pp. 673–676, 1988. (AVE 438).
Article: "Expandable Intraluminal Vascular Graft: A Feasibility Study," Surgery, vol. 99, pp. 199–205, 1986. (AVE 461).
Lawrence et al., Article: "Percutaneous Endovascular Graft: Experimental Evaluation." Radiology, vol. 163, pp. 357–360, 1987. (AVE 671).
Palmaz et al., Article: Expandable Intraluminal Graft: A Preliminary Study, Nov. 17–22, 1985, Radiology, vol. 156, pp. 73–77, 1985. (AVE 1224).
Fallone et al., "Elastic Characteristics of the Self–Expanding Metallic Stents," Investigative Radiology, vol. 23, pp. 370–76, 1988. (AVE 1953).
Palmaz Paper Entitled "Research Project Expandable Vascular Endoprosthesis".
Rousseau, et al., Publication: "Percutaneous Vascular Stent: Experimental Studies & Preliminary Clinical Results in Peripheral Arterial Diseases," in Inter. Angio, vol. 6, 153–161, 1987. (AVE 3301).
Rousseau, et al., Publication: "Self–Expanding Endovascular Prostesis: An Experimental Study," Radiology, vol. 164, pp. 709–714, 1987. (AVE 3303).
Wallace, et al., Article: "Tracheobronchial Tree: Expandable Metallic Stents Used in Experimental and Clinical Applications," Radiology, vol. 58, pp. 309–312, 1986. (DBX 2938).
Palmaz et al., Article: "Experimental Intraluminal Graft: A Preliminary Study," Radiology, vol. 156, pp. 73–77 (DBX 4595).
Program for the 12th Annual Course on Diagnostic Angiography and Interventional Radiology Mar. 23–26, 1987 sponsored by The Society of Cardiovascular and Interventional Radiology (DBX 6235).
Preliminary Motion for Judgment re: Wolff claims 1, 2–8, 10, 15 and 19 (DBX6759).
Palmaz Declaration (DBX 7069).
Letter from Gaterud to Dr. Palmaz dated Jul. 5, 1988 with attached document entitled: "Segmented, balloon–expandable stents." (DBX 7160).
Duprat et al., Article: "Flexible Balloon–Expandable Stent for Small Vessels," Radiology, vol. 168, pp. 276–278, 1987 (PX 82).
Drawing Sent to Bodic on Mar. 17, 1986 (PX 374).
Letter from Dr. Palmaz to R. Bowman enclosing a model of the flexible coronary graft dated Mar. 17, 1986 (PX 337).
Lab Notebook pages dated Jul. 30, 1987 from Rodney Wolff (COR 185596–597) (PX 621A).
Palmaz et al., Expandable Intraluminal Graft: A Preliminary Study Work in Progress, Radiology, vol. 156, No. 1, pp. 73–77, 1985. (API 33).

Charnsangavej, et al., Article: "Stenosis of The Vena Cava Prelimimnary Assessment of Treatment with expandable Metallic Stents," Radiology, vol. 161, No. 2, pp. 295–298 with attached photographs, 1986. (API 72).

J. Palmaz: The Current Status of Vascular Prostheses, published by SCIR in the Twelfth Annual Course on Diagnostic Angiography And Interventional Radiology Mar. 23–26, 1987. (API 73).

Amendment in Reponse to Office Action of Oct. 18, 1998 in re: Application of Julio Palmaz S/N 174,246. (API 152).

Article: Wallace, et al., Tracheobronchial Tree: Expandable Metallic Stents Used in Experimental and Clinical Applications Work In Progress, Radiology, vol. 158, pp. 309–312 . (API 295).

Reply of Senior Party Schatz To Patentee Wolff's Opposition To The Belated Motion For Judgment Of Applicant Schatz With Regard To Wolff Claims 1, 2–8, 10, 11, 13–17, And 19 (COR 186450–455) (API 310).

Brief Of Senior Party Schatz At Final Hearing (API 313).

Copy of Letter from Ron Sickles to Ben Tobor dated Feb. 10, 1988 (Exhibit 42).

Copy of Letter from R.O. Sickles to Mike Tatlow dated May 12, 1988 (Exhibit 43).

Copy of Letter from R. O. Sickles to Richard Schatz dated Jun. 2, 1988 (Exhibit 44).

Copy of Letter from Richard Schatz to Raimund Erbel dated Jun. 3, 1988 (Exhibit 45).

Copy of Letter from Richard Schatz to Mike Schuler dated Aug. 29, 1991 (Exhibit 48).

Minutes of J&J Stent Project Review Meeting dated Jan. 21, 1988 (Exhibit 7).

Preliminary Motion for Judgment with Regard to Wolff Claims 1, 2–8, 10, 11, 13–17, and 19. (Exhibit 67).

Declaration of Richard A Schatz. (Exhibit 75).

Belated Motion for Judgment with Regard to Wolff Claims 1, 2–8, 10, 11, 13–17 and 19. (Schatz—Exhibit 77).

Letter from Dr. Schatz to Mr. Tobor, dated Jun. 3, 1988. (Exhibit 122).

Letter from Dr. Schatz to Mr. Romano, dated Nov. 29, 1988. (Exhibit 131).

Letter from Mr. Sickles to Mr. Tobor, dated Feb. 10, 1988 (Exhibit 145).

Richard A. Schatz, Article titled: "A View of Vascular Stents" Circulation, vol. 79, No. 2, pp. 445–457, 1989. (Exhibit 194).

Senior Party Schatz's reply to Patentee Wolff's Opposition to the Preliminary Motion Of Applicant Schatz for judgement with regard to Wolff Claims 1, 2–8, 10, 11, and 13–17. (Exhibit 69).

Wallace, et al., Article: "Tracheobronchial Tree: Expandable Metallic Stents Used in Experimental and Clinical Applications[1] Work In Progress," Radiology, vol. 158, pp. 309–312, 1986. (Exhibit 165).

Charnsangavej, et al., Article: "Stenosis of The Vena Cava Prelimimnary Assessment of Treatment with expandable Metallic Stents," Radioloby, vol. 161, No. 2, pp. 295–298 with attached photographs, 1986. (Exhibit 167).

David D. Lawrence et al., Publication: Percutaneous Endovascular Graft: Experimental Evaluation[1], Radiology, pp. 163, 357–360, 1987. (Exhibit 173).

Charles E. Putnam, M.D., Cover and article from "Investigative Radiology", vol. 23. No. 5, May 1988. (Exhibit 177).

Robert N. Berk, Cover and article from "American Journal of Roentology", pp. 673–676, 1988. (Exhibit 178).

Declaration of John S. Kula Under 37 CFR § 1.672. (Kula—Exhibit 77).

Yoshioka et al., Article: "Self–Expanding Endovascular Graft: An Experimental Study in Dogs" AJR, vol. 151, pp. 673–676, 1988. (PX 100).

Palmaz, et al., Article: Expandable Intraluminal Graft: A Preliminary Study Work in Progress[1], Radiology, vol. 156, No. 1, pp. 73–77, 1985. (PX 101).

Declaration of Richard Schatz Under 37 C.F.R.§ 1.672. (PX 106).

Charnsangavej et al., Article: "Stenosis of the Vena Cave: Preliminary Assessment of Treatment with Expandable Metallic Stents," Radiology, vol. 161, pp. 295–298, 1986. (PX 143).

Wallace, et al., Article: Tracheobronchial Tree: Expandable Metallic Stents Used in Experimental and Clinical Applications Work in Progress[1], Radiology, vol. 158, pp. 309–312, 1986. (PX 144).

Gina Kolata, News Article: NY Times, "Devices That Opens Clogged Arteries Gets a Falling Grade in a New Study", pp. 16–18, Jan. 3, 1991. (PX 186).

Duprat, et al., Article: "Flexible Balloon–Expanded Stent for Small Vessels Work in Progress[1]", Radiology, vol. 162, pp. 276–278, 1987. (PX 207).

Letter from Palmaz to Bowman dated Mar. 17, 1986. (PX 350).

Memo re: Minutes of Stent Project Review—San Antonia—Mar. 15, 1988. (PX 651).

Kuntz, et al., Article: Clinical Cardiology Frontiers: "Defining Coronary Restenosis, Newer Clinical and Angiographic Paradigms", Circulation, Sep. 1993, vol. 88, No. 3, pp. 1310–1323. (PX 854).

Belated Motion for Judgment with regard to Wolff Claims1, 2–8, 10, 11, 13–17, and 19. (PX 1410).

Drawing of Sprial Stent (sent to Bodic Mar. 17, 1986). (PX 2933).

Wright et al., Article: Percutaneous Endovascular Stents: An Experimental Evaluation[1] Radiology, vol. 156, pp. 69–72, 1985. (PX 3093).

Charnsangavej et al., Article: "A New Expandable Metallic Stent for Dilation of Stenotic Tubular Structures: Experimental and Clinical Evaluation," Houston Medical Journal , vol. 3, pp. 41–51, 1987. (PX 3207).

In re Application of Wiktor, U.S. Appl. No. 69,636, Response to Office Action dated Mar. 17, 1988. (PX 3236).

Transmittal Letter of Response to First Office Action in '417 patent. (PX 3993).

Letter from B. Tobor ro R. Schatz dated Jul. 23, 1991. (PX 3996).

Mullins et al., Article: "Implantation of balloon–expandable intravascular grafts by catherization in pulmonary arteries and systemic veins," Circulation, vol. 77, No. 1, pp. 188–189, 1988. (PX 4049).

Schatz et al., Article: "Intravascular Stents for Angioplasty," Cardio, 1997. (PX 4050).

Schatz et al., Article: "New Technology in Angioplasty Balloon–Expandable Intravascular Stents, New Developments in Medicine," vol. 2, No. 2 pp. 59–75, 1987. (PX 4051).

Richard A. Schatz, Article: "Introduction to Intravascular Stents," Cardiology Clinics, vol. 6, No. 3, pp. 357–372, 1988. (PX 4052).

Richard A. Schatz, Article: "A View of Vascular Stents," Circulation, vol. 79, No. 2, pp. 445–457, 1989. (PX 4053).

Wang et al., Article: "An Update on Coronary Stents," Cardio, pp. 177–186, 1992. (PX 4054).

Richard A. Schatz, Article: "New Technology in Angioplasty: Balloon–Expandable Stents," Medicamundi, vol. 33, No. 3, pp. 112–116, 1988. (PX 4055).

Letter from Tobor to Schatz dated Sep. 29, 1988. (PX 1395).

Verified Statement of Facts by Unnamed Inventor R.A. Schatz document filed in U.S. Patent and Trademark Office on Sep. 8, 1989. (PX 3677).

Declaration of John S. Kula Under 37 CFR § 1.672 (Exhibit 329).

Letter to Mike Schular from R.A. Schatz dated Aug. 29, 1991. (Exhibit 402).

Articulated, Balloon—Expandable Stents, (DBX 7159).

J. Rösch et al., Experimental Intrahepatic Portacaval Anastomosis: Use of Expandable Gianturco Stents, Radiology, vol. 162, pp. 481–485, 1987.

J. Rösch et al., Modified Gianturco Expandable Wire Stents In Experimental and Clinical Use, Ann Radiol, vol. 31, No. 2, pp. 100–103, 1987.

J. Rösch et al., Gianturco Expandable Stents In the Treatment of Superior Vena Cava Syndrome Recurring After Vena Cava Syndrome Recurring After Maximum–Tolerance Radiation, Cancer, vol. 60, pp. 1243–1246, 1987.

J.E. Gordon, Structures or Why Things Don't Fall Down, Penguin Books, pp. 45–59, 132–148, 210–244, 377–383.

Maass et al., Radiological Follow–up of Transluminally Inserted Vascular Endoprostheses: An Experimental Study Using Expanding Spirals, Radiology, vol. 152, pp. 659–663, 1984.

Argument submitted re EP 86115473 dated Jan. 20, 1995. (AVE 2478).

Verified Statement of Facts by Julio C. Palmaz dated Aug. 4, 1989. (PX 3662).

Papanicolaou et al., Insertion of a Biliary Endoprosthesis Using A Balloon Dilatation Catheter, Gastrointest Radiology, vol. 10, pp. 394–396, 1985.

Palmaz et al., Expandable Intraluminal Vascular Graft: A Feasibility Study, Surgery, vol. 99, No. 2, pp. 199–205, 1986.

Palmaz et al., Atheroscierotic Rabbit Aortas: Expandable Intraluminal Grafting, Radiology, vol. 168, pp. 724–726, 1986.

Palmaz, The Current Status of Vascular Prostheses; Rësch et al., Gianturco, Expandable Stents in Experimental and Clinical Use, SCIVR, pp. 118–124, 1987.

Rösch et al., Abstract: Modified Gianturco Expandable Wire Stents in Experimental and Clinical Use, CIRSE, Porto Cervo, Sardinia, May 25–29, 1987.

Rösch et al., Gianturco Expandable Wire Stents in the Treatment of Superior Vena Cava Syndrome Recurring After Maximum–Tolerance Radiation, Cancer, vol. 60, pp. 1243–1246, 1987.

Mirich et al., Percutaneously Placed Endovascular Grafts for Aortic Aneurysms: Feasibility Study, Radiology, vol. 170, pp. 1033–1037, 1989.

Dotter, Transluminally–placed Coilspring Endarterial Tube Grafts, Investigative Radiology, vol. 4, Sep.–Oct., pp. 329–332, 1969.

Palmaz et al., Abstract: Expandable Intraluminal Graft: A Preliminary Study, Radiology, vol. 153 (P), Nov. 1983: 70th Scientific Assembly and Annual Meeting.

Cragg et al., Nonsurgical Placement of Arterial Endoprostheses: A New Technique Using Nitinol Wire, Radiology, vol. 147, pp. 261–263, Apr. 1983.

J. Rösch et al., Gianturco Expandable Stents in Experimental and Clinical Use, Program: "Twelfth Annual Course on Diagnostic Angiography and Interventional Radiology" (Society of Cardiovascular and Interventional Radiology, Pittsburgh, PA), Mar. 23–26, 1987 (the second Monofilament Article).

Uchida et al., Modifications of Gianturco Expandable Wire Stents, AJR, vol. 150, pp. 1185–1187, 1988.

Palmaz, Balloon–Expandable Intravascular Stent, AJR, vol. 1510, pp. 1263–1269.

*Cordis Corporation v. Advanced Cardiovascular Systems, Inc., Guidant Corporation, Arterial Vascular Engineering, Inc., Boston Scientific Corporation and SCIMED Life Systems, Inc.,* Plaintiff's Complaint, Oct. 23, 1997 (Case No. 97–550–SLR).

*Arterial Vascular Engineering, Inc. v. Cordis Corporation, Johnson & Johnson and Expandable–Grafts Partnership,* Plaintiff's First Amended Complaint for Declaratory Relief of Patent Validity, Unenforceability, Noninfringement, and for Antitrust Violations, Jan. 27, 1998 (Civil Action No. 97–700).

*Arterial Vascular Engineering, Inc. v. Cordis Corporation, Johnson & Johnson and Expandable–Grafts Partnership,* Cordis Corporation and Johnson & Johnson's Answer and Counterclaim, Feb. 27, 1998(Civil Action No. 97–700–SLR).

*Arterial Vascular Engineering, Inc. v. Cordis Corporation, Johnson & Johnson and Expandable–Grafts Partnership,* Expandable–Graft Partnership's Answer, Feb. 27, 1998 (Civil Action No. 97–700–SLR).

*Arterial Vascular Engineering, Inc. v. Cordis Corporation, Johnson & Johnson and Expandable–Grafts Partnership,* Reply of Plaintiff Arterial Vascular Engineering, Inc. To Counterclaims of Defendant Cordis Corporation, Mar. 31, 1998 (Civil Action No. 97–700–SLR).

*Arterial Vascular Engineering, Inc. v. Cordis Corporation, Johnson & Johnson and Expandable–Grafts Partnership,* Reply of Plaintiff Arterial Vascular Engineering, Inc. To Counterclaims of Defendant Expandable Grafts Partnership, Mar. 31, 1998 (Civil Action No. 97–700–SLR).

*Cordis Corporation v. Advanced Cardiovascular Systems, Inc. and Guidant Corporation,* Cordis Corporations's Motion for a Preliminary Injunction, Oct. 8, 1997 (Civil Action No. 97–550).

*Cordis Corporation v. Advanced Cardiovascular Systems, Inc., Guidant Corporation Arterial Vascular Engineering, Inc., Boston Scientific Corporation and SCIMED, Inc.,* Cordis's Motion for Preliminary Injunction Against Arterial Vascular Engineering, Inc., Dec. 29, 1997 (Case No. 97–550–SLR).

Deposition of R. Schatz, M.D. in *Cordis Corporation v. Advanced Cardiovascular Systems, Inc.,* taken on Jan. 8, 1998 (Civil Action No. 97–550 SLR).

Deposition of Lee P. Bendel in *Cordis Corporation v. Advanced Cardiovascular Systems, Inc.,* taken on Jan. 22, 1998 (Civil Action No. 97–550 SLR).

Deposition of Julio Cesar Palmaz in *Cordis Corporation v. Advanced Cardiovascular Systems, Inc.,* taken on Dec. 29, 1997 (Civil Action No. 97–550 SLR).

Deposition of Richard A. Bowman in *Cordis Corporation v. Advanced Cardiovascular Systems, Inc.*, taken on Jan. 9, 1998 (Civil Action No. 97–550 SLR).

Deposition of Gary Schneiderman in *Cordis Corporation v. Advanced Cardiovascular Systems, Inc.*, taken on Jan. 16, 1998 (Civil Action No. 97–550 SLR).

Deposition of David Pearle, M.D. in *Cordis Corporation v. Advanced Cardiovascular Systems, Inc.*, taken on Jul. 10, 1998 (Civil Action No. 97–550 SLR).

Preliminary Injunction hearing testimony taken on Feb. 9–13, 1998 (Civil Action No. 97–550 SLR).

*Cordis Corporation v. Advanced Cardiovascular Systems, Inc., et al.*, (Civil Action No. 97–550 SLR) and *Cordis Corporation v. Advanced Cardiovascular Systems, Inc., Et al.* (Civil Action No. 98–65–SLR), Opening Post Hearing Brief of Plaintiff Cordis Corporation in Support of Motion for Preliminary Injunction, Mar. 6, 1998 (Portions relevant to patent claim construction and patent validity issues).

*Cordis Corporation and Expandable Grafts Partnership v. Advanced Cardiovascular Systems, Inc. et al.*, Post–Hearing Reply Brief of Plaintiff Cordis Corporation in Support of Its Motion for Preliminary Injunction, Apr. 10, 1998 (Case No. 97–550 SLR) (Portions relevant to patent validity issues).

*Cordis Corporation and Expandable Grafts Partnership v. Advanced Cardiovascular Systems, Inc. et al.*, Plaintiff's Motion for a Preliminary Injunction Against Boston Scientific Corporation and SCIMED Life Systems, Inc. And Memorandum in Support, Apr. 13, 1998 (Case No. 97–550–SLR).

*Cordis Corporation and Expandable Grafts Partnership v. Advanced Cardiovascular Systems, Inc., et al.*, Judge Robinson's Order Denying Plaintiff's Motion for a Preliminary Injunction, Jul. 17, 1998 (Civil Action No. 97–550 SLR).

*Cordis Corporation and Expandable Grafts Partnership v. Advanced Cardiovascular Systems, Inc., et al.*, Defendant Boston Scientific Corporation and SCIMED Life Systems, Inc.'s Motion for Summary Judgment of Invalidity of U.S. Pat. No. 5,102,417, Aug. 27, 1998 (Civil Action No. 97–550–SLR).

*Boston Scientific Limited, et al. v. Expandable Grafts Partnership*, Plaintiffs' Statement of Claim, Mar. 13, 1997 (UK Action No. 1493).

*Boston Scientific Limited, et al. v. Expandable Grafts Partnership*, Defendant's Amended Defense and Counterclaim, Aug. 4, 1997 (UK Action No. 1493).

*Boston Scientific Limited, et al. v. Expandable Grafts Partnership*, Petition for Revocation, Mar. 13, 1997 (UK Action No. 1497).

*Boston Scientific Limited, et al. v. Expandable Grafts Partnership*, Particulars of Objections, Mar. 13, 1997 (UK Action No. 1497).

*Boston Scientific Limited, et al. v. Expandable Grafts Partnership* and *Boston Scientific Limited et al., v. Julio C. Palmaz*, Boston's Skeleton Argument (UK Action Nos. 1493, 1495, 1496, and 1497).

*Boston Scientific Limited, et al. v. Julio C. Palmaz and Expandable Grafts Partnership,* Skeleton Argument of Palmaz/EGP, Mar. 19, 1998 (UK Action Nos. 1493, 1495, 1496 and 1497).

*Boston Scientific Limited, et al. v. Julio C. Palmaz and Expandable Grafts Partnership,* EGP's Final Submissions, Apr. 2, 1998 (UK Action Nos. 1493, 1495, 1496 and 1497).

*Boston Scientific Limited, et al. v. Julio C. Palmaz and Expandable Grafts Partnership,* Judgment, Jun. 26, 1998 (UK Action Nos. 1493, 1495, 1496 and 1497).

Rösch, Modified Gianturco Expandable Wire Stents in Experimental and Clinical Use, CIRSE 1987 Presentation: see Witness Statement of Josef Rösch from U.K. Proceeding.

Statement of Claim by Boston Scientific et al. against Expandable Grafts Partnership et al., in *EPG et al., v. Boston Scientific et al.* in Netherlands (Mar. 13, 1997).

Motion for Joinder of Actions, Change of Claim and Statement of Claim filed by Expandable Grafts Partnership et al. in *EPG et al. v. Boston Scientific et al.* In Netherlands (Apr. 22, 1997).

Opinion of K.J. Metman filed in *EPG et al. v. Boston Scientific et al.* in Netherlands (Aug. 29, 1997).

Expert report of Dr. Nigel Buller in *EPG et al. v. Boston Scientific et al.* in Netherlands (Aug. 28, 1997).

Expert report of Lee P. Bendel in *EPG et al. v. Boston Scientific et al.* in Netherlands (Aug. 28, 1997).

Memorandum of Oral Pleading in *EPG et al. v. Boston Scientific et al.* in Netherlands (Sep. 12, 1997).

Plea Notes of P.A.M. in *EPG et al. v. Boston Scientific et al.* in Netherlands (Mar. 10, 1998).

Decision of Court of Appeals in *EPG et al. v. Boston Scientific et al.* in Netherlands (Apr. 23, 1998).

Translation of Nullity Action Against EPO 0 364 787 by Biotronik in Germany.

Translation of Nullity Action Against EPO 0 335 341 by Biotronik in Germany.

Translation of EPG Response to Nullity Action Against EP 0 364 787 by Biotronik in Germany.

Translation of EPG Response to Nullity Action EP 0 335 341 by Biotronik in Germany.

Nullity Suit Against EP–B1–0 335 341 Brought by Boston Scientific in Germany.

Translation of Opposition filed by Terumo Corp. Against Japan Patent No. 2680901.

Translation of Decision on Opposition Against Japan Patent No. 2680901.

Memorandum Order of the Court dated Sep. 7, 2000, concerning disputed claim construction.

Translation of Judgment in Nullity Action Against EP 0 364 787 by Biotronik in Germany.

Translation of Judgment in Nullity Action Against EP 0 335 341 by Biotronik in Germany.

Trial transcript from Mar. 17, 2005 at 171–172, 191–192.

Trial transcript from Mar. 18, 2005 at 282–285, 325–327, 349–351.

Trial transcript from Mar. 21, 2005 at 721–726.

Trial transcript from Mar. 24, 2005 at 1387.

*Cordis Corporation v. Medtronic Ave., Inc., et al.*, PROCEEDINGS, CA No. 97550 (SLR), etc., dated Jul. 26, 2001.

BSC's Opening Brief in Support of Its Motion for Judgment as a Matter of Law or, in the Alternative, for a New Trial.

Coris' Answering Brief in Opposition to BSC's Motion for JMOL or a New Trial on the Palmaz '762 Patent and the Schatz '332 Patents.

BSC's Reply Brief in Support of Its Motion for Judgment as a Matter of Law or, in the Alternative, for a New Trial.

J. Rösch et al., Abstract, Expandable Gianturco–Type Wire Stents in Experimental Intraheptic Portacaval Shunts, Program: "72nd Scientific Assembly and Annual Meeting of the Radiological Society of North America", Nov. 30–Dec. 5, 1986, Radiology, vol. 161, pp. 40–41, 1986.

Trial testimony transcripts from *Cordis Corporation v. Medtronic AVE* dated Mar. 4, 7–11 and 14, 2005.

Trial testimony transcripts from *Cordis Corporation v. Boston Scientific* dated Mar. 17, 18 and 21–24, 2005.

Trial testimony transcripts from the *cordis Corporation et al. v. Medtronic AVE, Inc., et al.* liability trial dated Nov. 6–9, 13–17 and 20–21, 2000.

Trial testimony transcripts from the *Cordis Corporation et al. v. Boston Scientific Corporation et al.* liability trial dated Nov. 21, Nov. 27–Dec. 1, Dec. 4–8 and Dec. 11, 2000.

Jury verdict form from the *Cordis Corporation et al. v. Medtronic AVE, Inc. et al.* liability trial.

Jury Verdict form from the *Cordis Corporation et al. v. Boston Scientific Corporation et al.* liability trial.

Hearing testimony transcript from the consolidated *Cordis Corporation et al. v. Medtronic AVE, Inc. et al. and Boston Scientific Corporation et al.* inequitable conduct hearing dated Feb. 7–9 and 12, 2001.

*Boston Scientific SCIMED, Inc. And Boston Scientific Corporation v. Cordis Corporation and Johnson and Johnson, Inc.,* Opening Expert Report of Stephen R. Hanson, Ph.D (Civil Action No. 03–283–SLR).

*Boston Scientific SCIMED, Inc. And Boston Scientific Corporation v. Cordis Corporation and Johnson and Johnson, Inc.,* Opening Expert Report of Robson F. Storey, Ph.D (Civil Action No. 03–283–SLR).

*Boston Scientific SCIMED, Inc. And Boston Scientific Corporation v. Cordis Corporation and Johnson and Johnson, Inc.,* Rebuttal Expert Report of Kinam Park, Ph.D. (Civil Action No. 03–283–SLR).

*Cordis Corporation v. Boston Scientific Corporation and SCIMED Life Systems, Inc.,* (C.A. No. 03–027–SLR) and *Boston Scientific SCIMED, Inc., and Boston Scientific Corporation v. Cordis Corporation and Johnson and Johnson and Johnson, Inc.* (C.A. No. 03–283–SLR) Combined Post–Hearing Brief In Support Of Cordis Corporation's Motion For Preliminary Injunction in C.A. No. 03–027–SLR, And In Opposition To Plaintiffs' Motion For Preliminary Injunction in C.A. No. 03–283–SLR.

*Cordis Corporation v. Boston Scientific Corporation and SCIMED Life Systems, Inc.,* (C.A. No. 03–027–SLR) and *Boston Scientific SCIMED, Inc., and Boston Scientific Corporation v. Cordis Corporation and Johnson and Johnson and Johnson, Inc.* (C.A. No. 03–283–SLR), Boston Scientific's Opening Post–Hearing Brief.

*Cordis Corporation v. Boston Scientific Corporation and SCIMED Life Systems, Inc.,* (C.A. No. 03–027–SLR) and *Boston Scientific SCIMED, Inc., and Boston Scientific Corporation v. Cordis Corporation and Johnson and Johnson and Johnson, Inc.* (C.A. No. 03–283–SLR), Combined Post–Hearing Answering Brief In Support of Cordis Corporations Motion For Preliminary Injunction In C.A. No. 03–027–SLR, And In Opposition To Plaintiff's Motion For Preliminary Injunction In C.A. No. 03–283–SLR.

Wu et al., Silicone–covered self–expanding metallic stents for the palliation of malignant esophageal obstruction and esophagorespiratory fistulas: experience in 32 patients and a review of the literature, *Gastrointestinal Endoscopy,* 1994, pp. 22–33, vol. 40, No. 1, Portland Oregan.

Binmoeller, et al., Silicone–Covered Expandable Metallic Stents in the Esophagus: An Experimental Study, Endoscopy, 1992, pp. 416–420, vol. 24, Georg Thieme Verlag Stuttgart New York.

*Boston Scientific SCIMED, Inc., and Boston Scientific Corporation v. Cordis Corporation and Johnson and Johnson, Inc.,* Answering Memorandum in Opposition to Plaintiff's Motion for a Preliminary Injunction (Civil Action No. 03–283–SLR).

*Boston Scientific SCIMED, Inc., and Boston Scientific Corporation v. Cordis Corporation and Johnson and Johnson, Inc.,* Plaintiffs Reply Brief in Support of Their Motion for Preliminary Injunction.

Rhine, Polymers for Sustained Macromolecule Release: Procedures to Fabricate Reproducible Delivery Systems and Control Release Kinetics, *Journal of Pharmaceutical Sciences,* 1980, pp. 265–270, vol. 69, No. 3.

Langer et al., Controlled Release of Macromolecules From Polymers, *Biomedical Polymers Polymeric Materials and Pharmaceuticals for Biomedical Use,* 1980, pp. 112–137, Academic Press, Inc. New York, NY.

Langer et al., Applications of Polymeric Delivery Systems for Macromolecules and Factors Controlling Release Kinetics.

Rhine et al., A Method to Achieve Zero–Order Release Kinetics From Polymer Matric Drug Delivey Systems, pp. 67–72.

Langer et al., Polymers for the Sustained Release of Macromolecules: Controlled and Magnetically Modulated Systems, *Better Therapy With Existing Drugs: New Uses and Delivery Systems;* 1981, pp. 179–216, Merck Sharp & Dohme International, Rahway, NJ.

Hsieh et al., Zero–Order Controlled–Release Polymer Matrices for Micro–and Macromolecules, *Journal of Pharmaceutical Sciences,* 1983, pp. 17–22, vol. 72, No. 1.

Brown et al., In Vivo and In Vitro Release of Macromolecules from Polymeric Drug Delivery Systems, *Journal of Pharmaceutical Sciences,* 1983, pp. 1181–1185, vol. 72, No. 10.

Langer, Implantable Controlled Release Systems, *Pharmac. Ther.,* 1983, pp. 35–51, vol. 21, printed in Great Britain.

Kost et al., Controlled Release of Bioactive Agents, *Trends in Biotechnology,* 1984, pp. 47–51, vol. 2, No. 2, Elseiver BV Amsterdam.

Bawa et al., An Explanation for the Controlled Release of Macromolecules from Polymers, *Journal of Controlled Release,* 1985, pp. 259–267, vol. 1. Elsevier Science BV Amsterdam.

Leong et al., Polymeric controlled drug delivery, 1987, pp. 199–233, vol. 1/3, Elsevier Science Publishers BV Amsterdam.

Langer, Polymeric Delivery Systems, *Targeting of Drugs 2 Optimization Strategies,* 1989, pp. 165–174, Plenum Press, New York and London.

Langer, Biomaterials in Controlled Drug Delivery: New Perspectives from Biotechnological Advances; *Pharmaceutical Technology,* 1989, pp. 18, 23–24, 26,28, 30.

Langer, Controlled Release Systems, pp. 115–124.

Laurencin et al., Polymeric Controlled Release Systems: New Methods for Drug Delivery, *Clinics in Laboratory Medicine,* 1987, pp. 301–323, vol. 7, No. 2, WB Saunders Company, Philadelphia.

Langer, Biopolymers in Controlled Release Systems, *Polymeric Biomaterials,* pp. 161–169.

Tsong–Pin Hsu et al., Polymers for the Controlled Release of Macromolecules: Effect of Molecular Weight of Ethylene–vinyl Acetate Copolymer, *Journal of Biomedical Materials Research*, 1985, pp. 445–460, vol. 19.

Langer, Polymers and Drug Delivery Systems, *Long–Acting Contraceptive Delivery Systems*, 1983, pp. 23–32, Harper & Row, Philadelphia, PA.

Langer, New Drug Delivery Systems: What the Clinician Can Expect, *Drug Therapy*, 1983, pp. 217–231.

Langer et al., Chemical and Physical Structure of Polymers as Carriers for Controlled Release of Bioactive Agents: A Review, *Rev. Macromol. Chem. Phys.*, 1983, pp. 61–126.

Langer, Polymeric Delivery Systems For Controlled Drug Release, *Chem. Eng. Commun.* 1980, pp. 1–48, vol. 6, Gordon and Breach Science Publishers, Inc. USA.

Langer et al., Biocompatibility of Polymeric Delivery Systems for Macromolecules, *Journal of Biomedical Materials Research*, 1981, pp. 267–277, vol. 15.

Langer, Controlled Release: A New Approach to Drug Delivery, *Technology Review*, 1981, pp. 26–34.

Langer et al., Sustained Release of Macromolecules from Polymers, *Polymeric Delivery Systems*, pp. 175–196, Gordon and Breach Science Publishers, New York.

Langer, Polymers for the Sustained Release of Proteins and other Macromolecules, *Nature*, 1976, pp. 797, 263, 799–800, vol. 263, No. 5580.

Alvarado, et al., Conducting of Polymer–Coated Expandable Stents In Bile Ducts, *Radiology*, 1989; 170:975–78.

Baker, et al., Controlled Release: Mechanisms and Rates (1974).

Hawson, et al., In Vivo Evaluation of Artificial Surfaces with a Nonhum Primate Model of Arterial Thrombosis, *J. Lab Clin. Med.*, Feb. 1980 pp. 289–304.

Baker, Controlled Release of Biologically Active Agents (1987) pp. 1–275.

*Cordis Corporation v. Boston Scientific Corporation* (CA. No. 03–27–SLR) and *Boston Scientific Scimed, Inc., v. Cordis Corporation and Johnson & Johnson, Incorporated* (CA. No. 03–283–SLR) Hearing Transcripts for Jul. 21, 2003, Jul. 22, 2003, Jul. 23, 2003 and Exhibits Thereto.

*Cords Corporation v. Advanced Cardiovascular Systems, Inc. et al.* (CA. No. 97–550–SLR), *Medtronic AVE, Inc. v. Cordis Corporation et al.* (CA. No. 97–700–SLR), *Boston Scientific Corporation v. Athicon, Inc. et al.* (CA No. 98–19–SLR), Expert Report of John T. Goolkasian, Esq.

*Cordis Corporation v. Advanced Cardiovascular Systems, Inc. et al.* (CA. No. 97–550–SLR), *Medtronic AVE, Inc. v. Cordis Corporation et al.* (CA. No. 97–700–SLR), *Boston Scientific Corporation v. Athicon, Inc. et al.* (CA No. 98–19–SLR), Expert Report of John F. Witherspoon.

*Cordis Corporation v. Boston Scientific Corporation et al.* (CA. No. 03–027–SLR), and *Boston Scientific Scimed, Inc. et al. v. Cordis Corporation et al.* (CA. No. 03–283–SLR), Boston Scientific's Post–Hearing Reply Brief.

*Cordis Corporation v. Boston Scientific Corporation et al.* (CA. No. 03–027–SLR), and *Boston Scientific Scimed, Inc. et al. v. Cordis Corporation et al.* (CA. No. 03–283–SLR), Memorandum Order.

*Cordis Corporation v. Boston Scientific Corporation et al.* (CA. No. 03–027–SLR), and *Boston Scientific Scimed, Inc. et al. v. Cordis Corporation et al.* (CA. No. 03–283–SLR), Deposition Transcript of Julio C. Palmaz.

*Cordis Corporation v. Advanced Cardiovascular Systems, Inc., Guidant Corporation, Arterial Vascular Engineering, Inc., Boston Scientific Corporation and SCIMED Life Systems, Inc.*, Defendants' Answer, Nov. 12, 1997 (Case No. 97–550–SLR).

*Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc.*, Answer and Counterclaims of Defendant Advanced Cardiovascular Systems, Inc., Apr. 8, 1998 (Case No. 97–550–SLR).

*Arterial Vascular Engineering, Inc. v. Cordis Corporation, Johnson & Johnson and Expandable Grafts Partnership,* Cordis Corporation and Johnson & Johnson's Answer and Counterclaim, Dec. 27, 1997 (Civil Action No. 97–700–SLR).

*Arterial Vascular Engineering, Inc. v. Cordis Corporation, Johnson & Johnson and Expandable Grafts Partnership,* Reply of Plaintiff Arterial Vascular Engineering, Inc., to Counterclaims of Defendant Cordis Corporation, Mar. 31, 1997 (Civil Action No. 97–700–SLR).

*Cordis Corporation and Expandable Grafts Partnership v. Advanced Cardiovascular Systems, Inc., et al*, Defendants ACS and Guidant's Motion For Summary Judgment, Aug. 27, 1998 (Civil Action No. 97–550–SLR).

*Cordis Corporation and Expandable Grafts Partnership v. Advanced Cardiovascular Systems, Inc., et al*, Plaintiffs' Answering Brief In Opposition To ACS's and BSC's Motion For Summary Judgment On Obviousness (Civil Action No. 97–550–SLR).

*Boston Scientific Limited et al. v. Expandable Grafts Partnership* and *Boston Scientific Limited et al. v. Julio C. Palmaz,* Boston's Closing Submissions (UK Action Nos. 1493, 1495, 1496 and 1497).

Plea Notes in *EPG et al. v. Boston Scientific et al.* in Netherlands (Sep. 12, 1997).

Provisional Judgment *EPG et al. v. Boston Scientific et al.* in Netherlands (Oct. 29, 1997).

Appeal filed by Expandable Grafts Partnership et al. in *EPG et al. v. Boston Scientific et al.* in Netherlands (Nov. 12, 1997).

Title filed by Boston Scientific et al. in *EPG et al. v. Boston Scientific et al.* in Netherlands (Jan. 22, 1998).

Statement of Rejoinder in the Action on the Merits, Also Including an Amendment of Defendants' Final Position in the Principal Action, as Well as the Provisional Statement of Rejoinder in the Action on the Counterclaim in *EPG et al. v Boston Scientific et al.* in Netherlands (Feb. 10, 1998).

Statement of Answer in the Ancillary Appeal in *EPG et al. v. Boston Scientific et al.* in Netherlands (Feb. 19, 1998).

*Cordis Corporation v. Boston Scientific,* Order Dated Mar. 27, 2006 (97–550–SLR).

*Cordis Corporation v. Boston Scientific,* Judgment in a Civil Case Dated Mar. 27, 2006 (97–550–SLR).

*Cordis Corporation v. Boston Scientific,* Memorandum Opinion Dated Mar. 27, 2006 (97–550–SLR).

*Cordis Corporation v. Boston Scientific,* Memorandum Opinion Dated Mar. 27, 2006 (97–550–SLR).

*Cordis Corporation v. Boston Scientific,* Memorandum Opinion Dated Mar. 27, 2006 (97–550–SLR).

*Cordis Corporation v. Boston Scientific,* Order Dated Mar. 27, 2006 (97–550–SLR).

*Cordis Corporation v. Boston Scientific,* Order Dated Mar. 27, 2006 (97–550–SLR).

Product Brochure, AVE Stents, no date.

*In re Am. Academy of Science Tech Center,* slip op. 03–1531 at 6–7 (Fed. Cir. May 13, 2004).
Mar. 11, 2005 Charge to the Jury.

Palmaz, J., et al., "*Expandable Intraheptic Portacaval Shunt Stents: Early Experience in the Dog,*" *AJR,* 145:821–825 (1985).

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–6 is confirmed.

* * * * *